United States Patent
Bhowmik et al.

(10) Patent No.: US 10,619,139 B2
(45) Date of Patent: Apr. 14, 2020

(54) THIOESTERASES AND THEIR USE

(71) Applicants: Givaudan S.A., Vernier (CH); Utah State University, North Logan, UT (US); Wisconsin Alumni Research Foundation, Madison, WI (US)

(72) Inventors: Tarun Bhowmik, Mason, OH (US); Jeff Broadbent, Amalga, UT (US); Dennis Welker, Logan, UT (US); James Steele, Cottage Grove, WI (US); Mateo Budinich, Las Condes Santiago (CL)

(73) Assignees: Givaudan SA, Vernier (CH); Utah State University, North Logan, UT (US); Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/050,493

(22) Filed: Jul. 31, 2018

(65) Prior Publication Data
US 2018/0355329 A1 Dec. 13, 2018

Related U.S. Application Data

(62) Division of application No. 13/824,060, filed as application No. PCT/EP2011/066644 on Sep. 26, 2011, now Pat. No. 10,066,219.

(60) Provisional application No. 61/386,173, filed on Sep. 24, 2010.

(51) Int. Cl.
| | |
|---|---|
| C12N 9/16 | (2006.01) |
| A23L 27/24 | (2016.01) |
| C12P 11/00 | (2006.01) |
| A23C 19/032 | (2006.01) |

(52) U.S. Cl.
CPC ............ *C12N 9/16* (2013.01); *A23C 19/0328* (2013.01); *A23L 27/25* (2016.08); *C12P 11/00* (2013.01); *C12Y 301/02* (2013.01); *G01N 2333/916* (2013.01)

(58) Field of Classification Search
CPC ....... A23C 19/0328; C12N 9/16; A23L 27/25; C12Y 301/02; G01N 2333/916; C12P 11/00
See application file for complete search history.

(56) References Cited

U.S. PATENT DOCUMENTS 8,119,385 B2 * 2/2012 Mathur .................... C12N 9/00
435/212

FOREIGN PATENT DOCUMENTS

WO  WO 2010/002890 A2  1/2010

OTHER PUBLICATIONS

Fenster et al., Characterization of an arylesterase from Lactobacillus helveticus CNRZ32. J. Appl. Microbiol. 2000, vol. 88: 572-583. (Year: 2000).
Broun et al., Catalytic plasticity of fatty acid modification enzymes underlying chemical diversity of plant lipids. Science, 1998, vol. 282: 1315-1317. (Year: 1998).
Devos et al., Practical limits of function prediction. Proteins: Structure, Function, and Genetics. 2000, vol. 41: 98-107. (Year: 2000).
Seffernick et al., Melamine deaminase and Atrazine chlorohydrolase: 98 percent identical buy functionally different. J. Bacteriol., 2001, vol. 183 (8): 2405-2410. (Year: 2001).
Whisstock et al., Prediction of protein function from protein sequence. Q. Rev. Biophysics., 2003, vol. 36 (3): 307-340. (Year: 2003).
Witkowski et al., Conversion of b-ketoacyl synthase to a Malonyl Decarboxylase by replacement of the active cysteine with glutamine. Biochemistry, 1999, vol. 38: 11643-11650. (Year: 1999).
PCT/EP2011/066644—International Search Report, dated Feb. 17, 2012.
PCT/EP2011/066644—International Written Opinion, dated Feb. 17, 2012.
Uniprot Consortium: "Sequence UPI0001BC2D0D", Nov. 13, 2009, XP055010998.
Brevibacterium linens BL2: COG0824: Predicted thioesterase [Brevibacterium linens BL2], Apr. 8, 2005, XP055010997.
Brevibacterium linens BL2: "Brevibacterium linens BL2 NZ_AAGP01000017, whole genome shotgun sequence", Apr. 6, 2004, XP055010996.
Brevibacterium linens BL2: "Brevibacterium linens BL2 2662183_Cont246, whole genome shotgun sequence", Apr. 7, 2005, XP055010993.
L. Marilley, "Flavours of cheese products: metabolic pathways, analytical tools and identification of producing strains", International Journal of Food Microbiology, vol. 90, No. 2; Jan. 15, 2004, pp. 139-159.
Curtin, et al., "Amino acid catabolism in cheese-related bacteria: Selection and study of the effects of ph, temperature and NaCL by quadratic response surface methodology", Journal of Applied Microbiology, Oxford, GB, Jan. 1, 2001, vol. 91, No. 2, pp. 312-321.
Engelvin, et al., "Identification of beta-oxidation and thioesterase activities in *Staphylococcus carnosus* 833 strain", FEMS Microbiology Letters 190, Jan. 1, 2000, pp. 115-120.
Mandrich, et al., "Alicyclobacillus acidocaldarius thermophilic esterase EST2's activity in milk and cheese models", Applied and Environmental Microbiology, May 1, 2006, pp. 3191-3197.

* cited by examiner

Primary Examiner — Ganapathirama Raghu
(74) Attorney, Agent, or Firm — Curatolo Sidoti Co., LPA; Salvatore A. Sidoti; Floyd Trillis, III

(57) ABSTRACT

Disclosed are nucleotide sequences encoding thioesterase enzymes, methods for their production, their use in methods to form thioesters, and their use in methods of screening for other wild type bacteria capable of producing said thioesterase enzymes. Also disclosed are compositions comprising thioesters produced by the methods disclosed herein.

19 Claims, No Drawings

Specification includes a Sequence Listing.

SEQUENCE LISTING

<160> NUMBER OF SEQ ID NOS: 27

<210> SEQ ID NO 1
<211> LENGTH: 408
<212> TYPE: DNA
<213> ORGANISM: Brevibacterium linens
<220> FEATURE:
<221> NAME/KEY: CDS

<222> LOCATION: (1)..(408)

<400> SEQUENCE: 1

| | | | | | | | | | | | | | | | | |
|---|---|---|---|---|---|---|---|---|---|---|---|---|---|---|---|---|
| ttg | tcc | gtg | aag | aca | ttc | gag | tat | tcc | cca | gag | gtg | cgt | tgg | tcc | gat | 48 |
| Leu | Ser | Val | Lys | Thr | Phe | Glu | Tyr | Ser | Pro | Glu | Val | Arg | Trp | Ser | Asp | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cag | gac | atg | ctt | ggc | cac | gtg | aac | aac | gcg | cgc | atg | atc | acc | ctc | atc | 96 |
| Gln | Asp | Met | Leu | Gly | His | Val | Asn | Asn | Ala | Arg | Met | Ile | Thr | Leu | Ile | |
| | | | 20 | | | | | 25 | | | | | 30 | | | |

| | | | | | | | | | | | | | | | | |
|---|---|---|---|---|---|---|---|---|---|---|---|---|---|---|---|---|
| gag | gag | tgc | cgc | atc | agg | tgg | ctc | cat | gaa | acc | gaa | gcg | ggc | agc | ctg | 144 |
| Glu | Glu | Cys | Arg | Ile | Arg | Trp | Leu | His | Glu | Thr | Glu | Ala | Gly | Ser | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| acc | ggc | ggg | ggc | atg | ctc | gtc | gcc | aac | cag | tcg | atc | gac | tac | ctg | ctc | 192 |
| Thr | Gly | Gly | Gly | Met | Leu | Val | Ala | Asn | Gln | Ser | Ile | Asp | Tyr | Leu | Leu | |
| | 50 | | | | | 55 | | | | | 60 | | | | | |

| | | | | | | | | | | | | | | | | |
|---|---|---|---|---|---|---|---|---|---|---|---|---|---|---|---|---|
| ccc | gtc | atg | tac | ggc | ccc | gag | ctc | aca | atg | acg | gtg | acc | gtc | aag | cgg | 240 |
| Pro | Val | Met | Tyr | Gly | Pro | Glu | Leu | Thr | Met | Thr | Val | Thr | Val | Lys | Arg | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| atc | ggc | agc | tcc | tcg | ttc | act | gtc | cac | acg | cgt | ggt | gac | cag | agc | ggc | 288 |
| Ile | Gly | Ser | Ser | Ser | Phe | Thr | Val | His | Thr | Arg | Gly | Asp | Gln | Ser | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| cag | aag | gtg | ttc | aac | tcc | gac | gtc | atc | ctc | gtc | cac | atc | gac | cgg | gaa | 336 |
| Gln | Lys | Val | Phe | Asn | Ser | Asp | Val | Ile | Leu | Val | His | Ile | Asp | Arg | Glu | |
| | | | | 100 | | | | | 105 | | | | | 110 | | |

| | | | | | | | | | | | | | | | | |
|---|---|---|---|---|---|---|---|---|---|---|---|---|---|---|---|---|
| acc | ggc | cga | cca | gca | ccg | atc | acc | gag | gac | att | cgc | agt | gtc | ctc | gag | 384 |
| Thr | Gly | Arg | Pro | Ala | Pro | Ile | Thr | Glu | Asp | Ile | Arg | Ser | Val | Leu | Glu | |
| | | | 115 | | | | | 120 | | | | | 125 | | | |

| | | | | | | | |
|---|---|---|---|---|---|---|---|
| gaa | tac | ggc | gcc | gag | gcc | ggc | tga | 408 |
| Glu | Tyr | Gly | Ala | Glu | Ala | Gly | | |
| | 130 | | | | | 135 | | |

<210> SEQ ID NO 2
<211> LENGTH: 135
<212> TYPE: PRT
<213> ORGANISM: Brevibacterium linens

<400> SEQUENCE: 2

Leu Ser Val Lys Thr Phe Glu Tyr Ser Pro Glu Val Arg Trp Ser Asp
1               5                   10                  15

Gln Asp Met Leu Gly His Val Asn Asn Ala Arg Met Ile Thr Leu Ile
            20                  25                  30

Glu Glu Cys Arg Ile Arg Trp Leu His Glu Thr Glu Ala Gly Ser Leu
        35                  40                  45

Thr Gly Gly Gly Met Leu Val Ala Asn Gln Ser Ile Asp Tyr Leu Leu
    50                  55                  60

Pro Val Met Tyr Gly Pro Glu Leu Thr Met Thr Val Thr Val Lys Arg
65                  70                  75                  80

Ile Gly Ser Ser Ser Phe Thr Val His Thr Arg Gly Asp Gln Ser Gly
                85                  90                  95

Gln Lys Val Phe Asn Ser Asp Val Ile Leu Val His Ile Asp Arg Glu
            100                 105                 110

Thr Gly Arg Pro Ala Pro Ile Thr Glu Asp Ile Arg Ser Val Leu Glu
        115                 120                 125

Glu Tyr Gly Ala Glu Ala Gly
    130                 135

<210> SEQ ID NO 3
<211> LENGTH: 603
<212> TYPE: DNA

<213> ORGANISM: Brevibacterium linens
<220> FEATURE:
<221> NAME/KEY: CDS
<222> LOCATION: (1)..(603)

<400> SEQUENCE: 3

```
gtg tgt tca cga tcc tat cgc ggc cct cac tgc agc ggt gaa ggt ggc      48
Val Cys Ser Arg Ser Tyr Arg Gly Pro His Cys Ser Gly Glu Gly Gly
 1               5                  10                  15 atg atg gga cat atg cac aac cgc acc acg aat ccc cat ctg aac gaa      96
Met Met Gly His Met His Asn Arg Thr Thr Asn Pro His Leu Asn Glu
             20                  25                  30 ttc aca cga gtc ctg ttg gaa ctg aga tgg gga gac atg gat gcc tat     144
Phe Thr Arg Val Leu Leu Glu Leu Arg Trp Gly Asp Met Asp Ala Tyr
         35                  40                  45 ggc cac gtc aac aat gtc acc cag ctg cgt ctg ctc gaa gag gca cgc     192
Gly His Val Asn Asn Val Thr Gln Leu Arg Leu Leu Glu Glu Ala Arg
     50                  55                  60 gtc cgc gct ctg ggc tca ccg acg cac agc acc gat gca ccc aca act     240
Val Arg Ala Leu Gly Ser Pro Thr His Ser Thr Asp Ala Pro Thr Thr
 65                  70                  75                  80 cca ggt cag ctg gga atc tca ggc acg gta tcg ggg atc aca att ccg     288
Pro Gly Gln Leu Gly Ile Ser Gly Thr Val Ser Gly Ile Thr Ile Pro
                 85                  90                  95 gcg atc ttc gcc gag gct tcg aac acc acc gag ctg ctc gtc gcc tcc     336
Ala Ile Phe Ala Glu Ala Ser Asn Thr Thr Glu Leu Leu Val Ala Ser
            100                 105                 110 cac gcg atc gaa tat cgc cgt ccc att ccc tac cgt gca ggt ccc att     384
His Ala Ile Glu Tyr Arg Arg Pro Ile Pro Tyr Arg Ala Gly Pro Ile
        115                 120                 125 gcc atc gat ctc gtc atc agc gag gtc aaa ccg gcc tct gtg acg atc     432
Ala Ile Asp Leu Val Ile Ser Glu Val Lys Pro Ala Ser Val Thr Ile
    130                 135                 140 ggt tac agc atc gcc gaa ccc gat ggt tcg gtc ggc tat acg ctg gca     480
Gly Tyr Ser Ile Ala Glu Pro Asp Gly Ser Val Gly Tyr Thr Leu Ala
145                 150                 155                 160 gag acg gtc atc gtc ttt gta gac agg acg acc tcc cga ccg cgt cgc     528
Glu Thr Val Ile Val Phe Val Asp Arg Thr Thr Ser Arg Pro Arg Arg
                165                 170                 175 ctg acc cag gag gag aca gca gca atg gaa gac gtc att cga cct gcc     576
Leu Thr Gln Glu Glu Thr Ala Ala Met Glu Asp Val Ile Arg Pro Ala
            180                 185                 190 gta ccg atg cgg ggt cgc aac cga tga                                 603
Val Pro Met Arg Gly Arg Asn Arg
        195                 200
```

<210> SEQ ID NO 4
<211> LENGTH: 200
<212> TYPE: PRT
<213> ORGANISM: Brevibacterium linens

<400> SEQUENCE: 4

```
Val Cys Ser Arg Ser Tyr Arg Gly Pro His Cys Ser Gly Glu Gly Gly
 1               5                  10                  15

Met Met Gly His Met His Asn Arg Thr Thr Asn Pro His Leu Asn Glu
             20                  25                  30

Phe Thr Arg Val Leu Leu Glu Leu Arg Trp Gly Asp Met Asp Ala Tyr
         35                  40                  45

Gly His Val Asn Asn Val Thr Gln Leu Arg Leu Leu Glu Glu Ala Arg
     50                  55                  60
```

```
Val Arg Ala Leu Gly Ser Pro Thr His Ser Thr Asp Ala Pro Thr Thr
 65                  70                  75                  80

Pro Gly Gln Leu Gly Ile Ser Gly Thr Val Ser Gly Ile Thr Ile Pro
                 85                  90                  95

Ala Ile Phe Ala Glu Ala Ser Asn Thr Thr Glu Leu Leu Val Ala Ser
            100                 105                 110

His Ala Ile Glu Tyr Arg Arg Pro Ile Pro Tyr Arg Ala Gly Pro Ile
        115                 120                 125

Ala Ile Asp Leu Val Ile Ser Glu Val Lys Pro Ala Ser Val Thr Ile
    130                 135                 140

Gly Tyr Ser Ile Ala Glu Pro Asp Gly Ser Val Gly Tyr Thr Leu Ala
145                 150                 155                 160

Glu Thr Val Ile Val Phe Val Asp Arg Thr Thr Ser Arg Pro Arg Arg
                165                 170                 175

Leu Thr Gln Glu Glu Thr Ala Ala Met Glu Asp Val Ile Arg Pro Ala
            180                 185                 190

Val Pro Met Arg Gly Arg Asn Arg
            195                 200

<210> SEQ ID NO 5
<211> LENGTH: 435
<212> TYPE: DNA
<213> ORGANISM: Brevibacterium linens
<220> FEATURE:
<221> NAME/KEY: CDS
<222> LOCATION: (1)..(435)

<400> SEQUENCE: 5 atg aat ccg cag tcg gac gca ctt cca gat gtc tca ctt gcc tca gcc      48
Met Asn Pro Gln Ser Asp Ala Leu Pro Asp Val Ser Leu Ala Ser Ala
  1               5                  10                  15 agc aac ttc gtc gcc gcc tcg ggg ctc gtc atc gac gag gtc acg aac      96
Ser Asn Phe Val Ala Ala Ser Gly Leu Val Ile Asp Glu Val Thr Asn
                 20                  25                  30 aca agc gtc cgc ggc cat gcc gat ctg ggc agc gac cac cac acg cct     144
Thr Ser Val Arg Gly His Ala Asp Leu Gly Ser Asp His His Thr Pro
            35                  40                  45 tgg ggc gtc gtc cac ggc ggt gtg tac aca acg ctc gtg gag agc acg     192
Trp Gly Val Val His Gly Gly Val Tyr Thr Thr Leu Val Glu Ser Thr
    50                  55                  60 gga agc att ggt gcc agc cac gct gtg ggc gag cgc ggc gag ttc gcc     240
Gly Ser Ile Gly Ala Ser His Ala Val Gly Glu Arg Gly Glu Phe Ala
 65                  70                  75                  80 gtc ggc atc cac aac gcc acc gac ttt ctg cgc ccg acc gcc ggc gcc     288
Val Gly Ile His Asn Ala Thr Asp Phe Leu Arg Pro Thr Ala Gly Ala
                 85                  90                  95 cgc gtt gca gtc gag ggc acc gcc ctg cat cag ggc cgg acc cag cag     336
Arg Val Ala Val Glu Gly Thr Ala Leu His Gln Gly Arg Thr Gln Gln
            100                 105                 110 ctg tgg gag gtc atc atc acc gac acc tca tcg gac aag gtc ctg gcc     384
Leu Trp Glu Val Ile Ile Thr Asp Thr Ser Ser Asp Lys Val Leu Ala
        115                 120                 125 cgc ggc cag ctg cgc ctg cag aac gtc ccc atg ccg aag gag gcc aac     432
Arg Gly Gln Leu Arg Leu Gln Asn Val Pro Met Pro Lys Glu Ala Asn
    130                 135                 140 tga                                                                  435

<210> SEQ ID NO 6
<211> LENGTH: 144
```

<212> TYPE: PRT
<213> ORGANISM: Brevibacterium linens

<400> SEQUENCE: 6

```
Met Asn Pro Gln Ser Asp Ala Leu Pro Asp Val Ser Leu Ala Ser Ala
1               5                   10                  15

Ser Asn Phe Val Ala Ala Ser Gly Leu Val Ile Asp Glu Val Thr Asn
            20                  25                  30

Thr Ser Val Arg Gly His Ala Asp Leu Gly Ser Asp His His Thr Pro
        35                  40                  45

Trp Gly Val Val His Gly Gly Val Tyr Thr Thr Leu Val Glu Ser Thr
    50                  55                  60

Gly Ser Ile Gly Ala Ser His Ala Val Gly Glu Arg Gly Glu Phe Ala
65                  70                  75                  80

Val Gly Ile His Asn Ala Thr Asp Phe Leu Arg Pro Thr Ala Gly Ala
                85                  90                  95

Arg Val Ala Val Glu Gly Thr Ala Leu His Gln Gly Arg Thr Gln Gln
            100                 105                 110

Leu Trp Glu Val Ile Ile Thr Asp Thr Ser Ser Asp Lys Val Leu Ala
        115                 120                 125

Arg Gly Gln Leu Arg Leu Gln Asn Val Pro Met Pro Lys Glu Ala Asn
    130                 135                 140
```

<210> SEQ ID NO 7
<211> LENGTH: 909
<212> TYPE: DNA
<213> ORGANISM: Brevibacterium linens
<220> FEATURE:
<221> NAME/KEY: CDS
<222> LOCATION: (1)..(909)

<400> SEQUENCE: 7

```
atg agc gat gca gaa ccc aca gcg gcc gag gcg aat gtc gac acg ctg    48
Met Ser Asp Ala Glu Pro Thr Ala Ala Glu Ala Asn Val Asp Thr Leu
1               5                   10                  15 cgc aaa gtg ctc gaa ctc gaa agt ctg agc ttc acc tcg gcg tct cgg    96
Arg Lys Val Leu Glu Leu Glu Ser Leu Ser Phe Thr Ser Ala Ser Arg
            20                  25                  30 gag agt gac tac ttc ctc gga cag aat cag tac aaa ccc gat ggg cgc   144
Glu Ser Asp Tyr Phe Leu Gly Gln Asn Gln Tyr Lys Pro Asp Gly Arg
        35                  40                  45 gtc tac ggc ggt cag gtc gtg gcg caa tct gtg gtg gcc gct gcc gcg   192
Val Tyr Gly Gly Gln Val Val Ala Gln Ser Val Val Ala Ala Ala Ala
    50                  55                  60 acc ctg ccg gat gat cgc ctc atc cat tca ctt cac ggc tat ttc ctt   240
Thr Leu Pro Asp Asp Arg Leu Ile His Ser Leu His Gly Tyr Phe Leu
65                  70                  75                  80 cgt gcc ggg gat gtc agc gaa ccg atc gag ttc ggt gtc gaa cga ctc   288
Arg Ala Gly Asp Val Ser Glu Pro Ile Glu Phe Gly Val Glu Arg Leu
                85                  90                  95 cgt gac ggg cga tcg ttc tcc gct cgg cgt gtc cac gcc tat cag aag   336
Arg Asp Gly Arg Ser Phe Ser Ala Arg Arg Val His Ala Tyr Gln Lys
            100                 105                 110 gat gtg cct atc ctg tcc ttg atc gcc tct ttc caa gtc gag cag gag   384
Asp Val Pro Ile Leu Ser Leu Ile Ala Ser Phe Gln Val Glu Gln Glu
        115                 120                 125 ggc ctt gaa cac gct gag acc atg cca tcg ggt ctg ccc ggt cca ctg   432
Gly Leu Glu His Ala Glu Thr Met Pro Ser Gly Leu Pro Gly Pro Leu
    130                 135                 140
```

```
gag tgc ccg gag ctg cga gac att ctc gca gga cag gac aca cca cag      480
Glu Cys Pro Glu Leu Arg Asp Ile Leu Ala Gly Gln Asp Thr Pro Gln
145                 150                 155                 160 gtc act gaa tgg ctg aat aag cga ccc ttc gag atc cgt ccg gtc gaa      528
Val Thr Glu Trp Leu Asn Lys Arg Pro Phe Glu Ile Arg Pro Val Glu
                165                 170                 175 gcg tcc ctg tat ctc acc tcc acc gat gac cgc cag cgc gaa cgg cag      576
Ala Ser Leu Tyr Leu Thr Ser Thr Asp Asp Arg Gln Arg Glu Arg Gln
            180                 185                 190 cac gtt tgg ttc cgc gcc agc tcg ccc ttc ggc gat gat ccg gtg ctc      624
His Val Trp Phe Arg Ala Ser Ser Pro Phe Gly Asp Asp Pro Val Leu
        195                 200                 205 aat gct gct gca ctg gcc tat gcc agc gac ttc aac ctg ctc gaa ccg      672
Asn Ala Ala Ala Leu Ala Tyr Ala Ser Asp Phe Asn Leu Leu Glu Pro
    210                 215                 220 gtt ctg cgc cgt cag gga ctg agt tgg acg agt ccg ggg ctc cgg gtg      720
Val Leu Arg Arg Gln Gly Leu Ser Trp Thr Ser Pro Gly Leu Arg Val
225                 230                 235                 240 gcc agc ctc gac cac gcg atg tgg tgg cat cgt cgg gtc cgg gtc gat      768
Ala Ser Leu Asp His Ala Met Trp Trp His Arg Arg Val Arg Val Asp
                245                 250                 255 gag tgg atg ctc tat gtt cag gag tct cct gcc gcc cag gga ggc cgc      816
Glu Trp Met Leu Tyr Val Gln Glu Ser Pro Ala Ala Gln Gly Gly Arg
            260                 265                 270 ggt ctc ggc tac ggg cgg atc ttc gcc cag acg ggc gag ctg ctg gca      864
Gly Leu Gly Tyr Gly Arg Ile Phe Ala Gln Thr Gly Glu Leu Leu Ala
        275                 280                 285 aca gtg gct caa gag ggc atg gtc cgt gtg aag gct ccg cag tga          909
Thr Val Ala Gln Glu Gly Met Val Arg Val Lys Ala Pro Gln
    290                 295                 300

<210> SEQ ID NO 8
<211> LENGTH: 302
<212> TYPE: PRT
<213> ORGANISM: Brevibacterium linens

<400> SEQUENCE: 8

Met Ser Asp Ala Glu Pro Thr Ala Ala Glu Ala Asn Val Asp Thr Leu
1               5                   10                  15

Arg Lys Val Leu Glu Leu Glu Ser Leu Ser Phe Thr Ser Ala Ser Arg
            20                  25                  30

Glu Ser Asp Tyr Phe Leu Gly Gln Asn Gln Tyr Lys Pro Asp Gly Arg
        35                  40                  45

Val Tyr Gly Gly Gln Val Ala Gln Ser Val Ala Ala Ala Ala
    50                  55                  60

Thr Leu Pro Asp Asp Arg Leu Ile His Ser Leu His Gly Tyr Phe Leu
65                  70                  75                  80

Arg Ala Gly Asp Val Ser Glu Pro Ile Glu Phe Gly Val Glu Arg Leu
                85                  90                  95

Arg Asp Gly Arg Ser Phe Ser Ala Arg Arg Val His Ala Tyr Gln Lys
            100                 105                 110

Asp Val Pro Ile Leu Ser Leu Ile Ala Ser Phe Gln Val Glu Gln Glu
        115                 120                 125

Gly Leu Glu His Ala Glu Thr Met Pro Ser Gly Leu Pro Gly Pro Leu
    130                 135                 140

Glu Cys Pro Glu Leu Arg Asp Ile Leu Ala Gly Gln Asp Thr Pro Gln
145                 150                 155                 160

Val Thr Glu Trp Leu Asn Lys Arg Pro Phe Glu Ile Arg Pro Val Glu
```

```
                        165                 170                 175
Ala Ser Leu Tyr Leu Thr Ser Thr Asp Asp Arg Gln Arg Glu Arg Gln
            180                 185                 190

His Val Trp Phe Arg Ala Ser Ser Pro Phe Gly Asp Asp Pro Val Leu
            195                 200                 205

Asn Ala Ala Leu Ala Tyr Ala Ser Asp Phe Asn Leu Leu Glu Pro
    210                 215                 220

Val Leu Arg Arg Gln Gly Leu Ser Trp Thr Ser Pro Gly Leu Arg Val
225                 230                 235                 240

Ala Ser Leu Asp His Ala Met Trp Trp His Arg Val Arg Val Asp
            245                 250                 255

Glu Trp Met Leu Tyr Val Gln Glu Ser Pro Ala Ala Gln Gly Gly Arg
            260                 265                 270

Gly Leu Gly Tyr Gly Arg Ile Phe Ala Gln Thr Gly Glu Leu Leu Ala
            275                 280                 285

Thr Val Ala Gln Glu Gly Met Val Arg Val Lys Ala Pro Gln
    290                 295                 300
```

<210> SEQ ID NO 9
<211> LENGTH: 17
<212> TYPE: DNA
<213> ORGANISM: Artificial sequence
<220> FEATURE:
<223> OTHER INFORMATION: Synthetic sequence

<400> SEQUENCE: 9
aggaggatta acatatg                                                    17

<210> SEQ ID NO 10
<211> LENGTH: 45
<212> TYPE: DNA
<213> ORGANISM: Artificial sequence
<220> FEATURE:
<223> OTHER INFORMATION: Primer

<400> SEQUENCE: 10
gaattctaga aggaggatta acatatgtcc gtgaagacat tcgag                     45

<210> SEQ ID NO 11
<211> LENGTH: 33
<212> TYPE: DNA
<213> ORGANISM: Artificial sequence
<220> FEATURE:
<223> OTHER INFORMATION: Primer

<400> SEQUENCE: 11
agatctgtcg acgccggcct cggcgccgta ttc                                  33

<210> SEQ ID NO 12
<211> LENGTH: 49
<212> TYPE: DNA
<213> ORGANISM: Artificial sequence
<220> FEATURE:
<223> OTHER INFORMATION: Primer

<400> SEQUENCE: 12
caattgtcta gaaggaggat taacatatgt gttcacgatc ctatcgcgg                 49

<210> SEQ ID NO 13
<211> LENGTH: 34
<212> TYPE: DNA
<213> ORGANISM: Artificial sequence

```
<220> FEATURE:
<223> OTHER INFORMATION: Primer

<400> SEQUENCE: 13
agatctctcg agtcggttgc gaccccgcat cggt                        34

<210> SEQ ID NO 14
<211> LENGTH: 47
<212> TYPE: DNA
<213> ORGANISM: Artificial sequence
<220> FEATURE:
<223> OTHER INFORMATION: Primer

<400> SEQUENCE: 14
gaattctcta gaaggaggat taacatatga atccgcagtc ggacgca          47

<210> SEQ ID NO 15
<211> LENGTH: 35
<212> TYPE: DNA
<213> ORGANISM: Artificial sequence
<220> FEATURE:
<223> OTHER INFORMATION: Primer

<400> SEQUENCE: 15
agatctctcg aggttggcct ccttcggcat gggga                       35

<210> SEQ ID NO 16
<211> LENGTH: 46
<212> TYPE: DNA
<213> ORGANISM: Artificial sequence
<220> FEATURE:
<223> OTHER INFORMATION: Primer

<400> SEQUENCE: 16
gaattctaga aggaggatta acatatgagc gatgcagaaac ccacag          46

<210> SEQ ID NO 17
<211> LENGTH: 33
<212> TYPE: DNA
<213> ORGANISM: Artificial sequence
<220> FEATURE:
<223> OTHER INFORMATION: Primer

<400> SEQUENCE: 17
agatctctcg agctgcggag ccttcacacg gac                         33

<210> SEQ ID NO 18
<211> LENGTH: 803
<212> TYPE: DNA
<213> ORGANISM: Artificial sequence
<220> FEATURE:
<223> OTHER INFORMATION: Combined promoter and TE gene construct

<400> SEQUENCE: 18
caggctcacc acgtcgctga gtccggagaa ttcgggaccg gtcacatctg cccgttcgct    60
catcactccc ctttgctcaa cattgtggcc ttcgctggcc gttcctttca ctctattatc   120
ctctcccacg gcaggcccgc accgacaggc accgcaattg tggaatatct gggttcaacc   180
gctctagaat aggaggcacc atgtgttcac gatcctatcg cggccctcac tgcagcggtg   240
aaggtggcat gatgggacat atgcacaacc gcaccacgaa tccccatctg aacgaattca   300
cacgagtcct gttggaactg agatggggag acatggatgc ctatggccac gtcaacaatg   360
tcacccagct gcgtctgctc gaagaggcac gcgtccgcgc tctgggctca ccgacgcaca   420
```

```
gcaccgatgc acccacaact ccaggtcagc tgggaatctc aggcacggta tcggggatca    480
caattccggc gatcttcgcc gaggcttcga acaccaccga gctgctcgtc gcctcccacg    540
cgatcgaata tcgccgtccc attccctacc gtgcaggtcc cattgccatc gatctcgtca    600
tcagcgaggt caaaccggcc tctgtgacga tcggttacag catcgccgaa cccgatggtt    660
cggtcggcta tacgctggca gagacggtca tcgtctttgt agacaggacg acctcccgac    720
cgcgtcgcct gacccaggag gagacagcag caatggaaga cgtcattcga cctgccgtac    780
cgatgcgggg tcgcaaccga tga                                           803

<210> SEQ ID NO 19
<211> LENGTH: 803
<212> TYPE: DNA
<213> ORGANISM: Artificial sequence
<220> FEATURE:
<223> OTHER INFORMATION: Combined promoter and TE gene construct

<400> SEQUENCE: 19
gtctcccgtc tgatcgccgg cagcaacgag atccaggaga tcgagatcaa cccggtgcgc     60
gtgaccccgg atggggcatt ggccgtcgac gcgctcgtcg tcacgaaccg agacgacaac    120
gatggcagca ccgacaacga cagcggcagc gacaaccccg acaacgacag cagcaccgac    180
aaccccgaca aggaggcacc atgtgttcac gatcctatcg cggccctcac tgcagcggtg    240
aaggtggcat gatgggacat atgcacaacc gcaccacgaa tccccatctg aacgaattca    300
cacgagtcct gttggaactg agatggggag acatggatgc ctatggccac gtcaacaatg    360
tcacccagct gcgtctgctc gaagaggcac gcgtccgcgc tctgggctca ccgacgcaca    420
gcaccgatgc acccacaact ccaggtcagc tgggaatctc aggcacggta tcggggatca    480
caattccggc gatcttcgcc gaggcttcga acaccaccga gctgctcgtc gcctcccacg    540
cgatcgaata tcgccgtccc attccctacc gtgcaggtcc cattgccatc gatctcgtca    600
tcagcgaggt caaaccggcc tctgtgacga tcggttacag catcgccgaa cccgatggtt    660
cggtcggcta tacgctggca gagacggtca tcgtctttgt agacaggacg acctcccgac    720
cgcgtcgcct gacccaggag gagacagcag caatggaaga cgtcattcga cctgccgtac    780
cgatgcgggg tcgcaaccga tga                                           803

<210> SEQ ID NO 20
<211> LENGTH: 635
<212> TYPE: DNA
<213> ORGANISM: Artificial sequence
<220> FEATURE:
<223> OTHER INFORMATION: Combined promoter and TE gene construct

<400> SEQUENCE: 20
caggctcacc acgtcgctga gtccggagaa ttcgggaccg gtcacatctg cccgttcgct     60
catcactccc ctttgctcaa cattgtggcc ttcgctggcc gttcctttca ctctattatc    120
ctctcccacg gcaggcccgc accgacaggc accgcaattg tggaatatct gggttcaacc    180
gctctagaat aggaggcacc atgaatccgc agtcggacgc acttccagat gtctcacttg    240
cctcagccag caacttcgtc gccgcctcgg ggctcgtcat cgacgaggtc acgaacacaa    300
gcgtccgcgg ccatgccgat ctgggcagcg accaccacac gccttggggc gtcgtccacg    360
gcggcgtgta cacaacgctc gtggagagca cgggaagcat tggtgccagc cacgctgtgg    420
gcgagcgcgc cgagttcgcc gtcggcatcc acaacgccac cgactttctg cgcccgaccg    480
ccggcgcccg cgttgcagtc gagggcaccg ccctgcatca gggccggacc cagcagctgt    540
```

```
gggaggtcat catcaccgac acctcatcgg acaaggtcct ggcccgcggc cagctgcgcc    600
tgcagaacgt ccccatgccg aaggaggcca actga                              635
```

<210> SEQ ID NO 21
<211> LENGTH: 635
<212> TYPE: DNA
<213> ORGANISM: Artificial sequence
<220> FEATURE:
<223> OTHER INFORMATION: Combined promoter and TE gene construct

<400> SEQUENCE: 21

```
gtctcccgtc tgatcgccgg cagcaacgag atccaggaga tcgagatcaa cccggtgcgc     60
gtgaccccgg atgggcatt ggccgtcgac gcgctcgtcg tcacgaaccg agacgacaac    120
gatggcagca ccgacaacga cagcggcagc gacaaccccg acaacgacag cagcaccgac    180
aaccccgaca aggaggcacc atgaatccgc agtcggacgc acttccagat gtctcacttg    240
cctcagccag caacttcgtc gccgcctcgg ggctcgtcat cgacgaggtc acgaacacaa    300
gcgtccgcgg ccatgccgat ctgggcagcg accaccacac gccttggggc gtcgtccacg    360
gcggcgtgta cacaacgctc gtggagagca cgggaagcat tggtgccagc cacgctgtgg    420
gcgagcgcgg cgagttcgcc gtcggcatcc acaacgccac cgactttctg cgcccgaccg    480
ccggcgcccg cgttgcagtc gagggcaccg ccctgcatca gggccggacc cagcagctgt    540
gggaggtcat catcaccgac acctcatcgg acaaggtcct ggcccgcggc cagctgcgcc    600
tgcagaacgt ccccatgccg aaggaggcca actga                              635
```

<210> SEQ ID NO 22
<211> LENGTH: 27
<212> TYPE: DNA
<213> ORGANISM: Artificial sequence
<220> FEATURE:
<223> OTHER INFORMATION: Primer

<400> SEQUENCE: 22

```
gttatctaga cgatttctta tggagag                                        27
```

<210> SEQ ID NO 23
<211> LENGTH: 38
<212> TYPE: DNA
<213> ORGANISM: Artificial sequence
<220> FEATURE:
<223> OTHER INFORMATION: Primer

<400> SEQUENCE: 23

```
gtttagatct cttcctttcc aatttgtcca ctcaccag                            38
```

<210> SEQ ID NO 24
<211> LENGTH: 39
<212> TYPE: DNA
<213> ORGANISM: Artificial sequence
<220> FEATURE:
<223> OTHER INFORMATION: Primer

<400> SEQUENCE: 24

```
gtttagatct catgaatccg cagtcggacg cacttccag                           39
```

<210> SEQ ID NO 25
<211> LENGTH: 34
<212> TYPE: DNA
<213> ORGANISM: Artificial sequence
<220> FEATURE:

-continued

```
<223> OTHER INFORMATION: Primer

<400> SEQUENCE: 25
gtttggatcc tcgaatcagt gcccatctca gttg                               34

<210> SEQ ID NO 26
<211> LENGTH: 35
<212> TYPE: DNA
<213> ORGANISM: Artificial sequence
<220> FEATURE:
<223> OTHER INFORMATION: Primer

<400> SEQUENCE: 26
gtttagatct gcgtgtgttc acgatcctat cgcgg                              35

<210> SEQ ID NO 27
<211> LENGTH: 36
<212> TYPE: DNA
<213> ORGANISM: Artificial sequence
<220> FEATURE:
<223> OTHER INFORMATION: Primer

<400> SEQUENCE: 27
gtttggatcc agtcatcggt tgcgaccccg catcgg                             36
```

THIOESTERASES AND THEIR USE

The present application is a divisional of co-pending U.S. Ser. No. 13/824,060, filed Apr. 10, 2014, now U.S. Pat. No. 10,066,219, which is a national stage application of International Application No. PCT/EP2011/066644, filed Sep. 26, 2011, which claims priority from U.S. Provisional Patent Application No. 61/386,173, filed Sep. 24, 2010, and which are incorporated herein by reference.

TECHNICAL FIELD

Disclosed are nucleotide sequences encoding thioesterase enzymes, methods of their production, and their use in methods of forming thioesters.

BACKGROUND

Thioesters are important flavouring compounds for, amongst other things, cheese, vegetable, meat and coffee products. Particularly useful thioesters include, but are not limited to, methyl butanethioate, (hereinafter "MTB"), methyl thioacetate (hereinafter "MTA") and methyl thiopropionate (hereinafter "MTP").

Thioesters can be made synthetically. However, because of food trends, and health and wellness concerns, there is particular demand for flavour compounds, such as thioesters, that are either obtained directly from natural products, or produced via biological processes. A particular advantage of such compounds is that they may be termed "natural" and potentially labeled as such on consumable products.

It is known that various bacteria produce thioesters during fermentation. However, the yields and product ratios of these existing processes are difficult to influence.

Accordingly, it would be beneficial to develop a more predictable and potentially more economically viable method of producing thioesters that could be used in consumable products and labeled as "natural".

DETAILED DESCRIPTION

The applicant has now identified nucleotide sequences encoding thioesterase enzymes.

This finding enables the nucleotide sequences to be used in methods enabling the efficient production of thioesters that can be added to consumable products and labeled as "natural". Furthermore, these nucleotide sequences may be used in screening methods to identify other wild type bacteria capable of forming thioesters.

According to a first illustrative embodiment, there are provided nucleotide sequences, encoding enzymes having thioesterase activity comprising the nucleotide sequences, or functional equivalents thereof, disclosed in SEQ. ID. Nos. 1, 3, 5, and 7.

Without limitation, and only by way of illustration, the nucleic acids may be isolated from bacteria belonging to the *Brevibacterium* family. According to certain embodiments, the nucleic acids may be isolated from bacteria belonging to the *Brevibacterium* Linens species, a non limiting examples is strain American type culture collection (herein after ATCC) 9174 (BL2).

Functional equivalents of the nucleotide sequences include those nucleotide sequences that by virtue of the degeneracy of the genetic code possess a different nucleotide sequence to those disclosed herein, but that encode the same amino acid sequence with the same activity.

Functional equivalents encompass naturally occurring variants of the sequences described herein as well as synthetic nucleotide sequences, e.g., those nucleotide sequences that are obtained by chemical synthesis or recombination of naturally existing DNA. Functional equivalents may be the result of, natural or synthetic substitutions, additions, deletions, replacements, or insertions of one or more nucleotides.

Examples of functional equivalents include those nucleic acid sequences comprising a sense mutation resulting from the substitution of at least one conserved amino acid which does not lead to an alteration in the activity of the polypeptide, and thus can be considered functionally neutral.

Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (1); 5) Isoleucine (I), Leucine (L), Methionine (M), Valine (V); and 6) Phenylalanine (F), Tyrosine (Y), Tryptophan (W). Another alternative guideline is to allow for all charged amino acids as conservative substitutions for each other whether they are positive or negative.

Individual substitutions, deletions or additions that alter, add or delete a single amino acid or a small percentage (for example up to 26%, up to 20%, up to 10%, or up to 5%) of amino acids in an encoded sequence are also considered to be functional equivalents.

Other non-limiting examples of functional equivalents include fragments, orthologs, splice variants, single nucleotide polymorphisims, and allelic variants.

Such functional equivalents will have 60%, 75%, 80%, 90%, 95% or greater homology to the nucleotide sequences disclosed herein.

Nucleotide sequence homology may be determined by sequence identity or by hybridisation.

Sequence identity may be determined using basic local alignment search tool technology (hereinafter BLAST). BLAST technology is a heuristic search algorithm employed by the programs blastn.

If homology is determined by hybridisation, the nucleotide sequences should be considered substantially homologous provided that they are capable of selectively hybridizing to the nucleotide sequences disclosed herein.

Hybridisation should be carried out under stringent hybridisation conditions at a temperature of 42° C. in a solution consisting of 50% formamide, 5× standard sodium citrate (hereinafter SSC), and 1% sodium dodecyl sulphate (hereinafter SDS). Washing may be carried out at 65° C. in a solution of 0.2×SSC and 0.1% SDS.

Background hybridization may occur because of other nucleotide sequences present, for example, in the cDNA. Any signal that is less than 10 fold as intense as the specific interaction observed with the target DNA should be considered background. The intensity of interaction may be measured, for example, by radiolabelling the probe, e.g. with 32P.

The nucleotide sequences may also comprise one or more of the following: a suitable 5' untranslated region, a promoter to enable expression in appropriate host cells, a suitable 3' untranslated region, a stop codon and tags.

Non limiting examples of tags include, but are not limited to, membrane export tags and tags used for detection of the thioesterases including, but not limited to, His tag, glutathione-S-transferase tag (GST).

The 5' untranslated region may comprise other operators or motifs that influence the efficiency of transcription or translation. The 3' untranslated region may comprise other signals such as a signal for transcriptional termination.

Non limiting examples of operators or motifs that influence transcription or translation include, but are not limited to, signals required for efficient polydenylation of the transcript, ribosome binding sites, recognition sites e.g. EcoR1.

It is well within the purview of the person skilled in the art to select suitable 5' and 3' untranslated regions, tags, stop codons, and operators or motifs that influence transcription or translation, depending on the host cells in question and the desired result. Non limiting examples are given in the examples included herein.

The nucleotide sequences disclosed in SEQ. ID. Nos. 1, 3, 5, and 7, or functional equivalents thereof, may be used to produce thioesterase enzymes comprising the amino acid sequences disclosed in SEQ. ID. Nos. 2, 4, 6, and 8, or functional equivalents thereof.

Expression of the enzymes with thioesterase activity comprising one or more of the amino acid sequences, or functional equivalents thereof, disclosed in SEQ. ID. Nos. 2, 4, 6, and 8, may be effected by well established cloning techniques.

According to another illustrative embodiment, there is provided a host cell transfected with one or more of the nucleotide sequences disclosed in SEQ. ID. Nos. 1, 3, 5, and 7, or functional equivalent thereof. Such host cells are capable of expressing an enzyme with thioesterase activity comprising one or more of the amino acid sequences, or functional equivalents thereof, disclosed in SEQ. ID. Nos. 2, 4, 6, and 8.

Suitable host cells include prokaryote and eukaryotic cells of bacterial, fungal, plant or animal origin.

According to an illustrative embodiment the cells are bacterial or fungal cells.

In another illustrative embodiment the cells are selected from one or more of *Escherichia coli, Brevibacterium, Cornynebacterium, Arthrobacter, Pseudomonas, Nocardia, Methylobacteri, Lactobacillus, Lactococcus, Streptococcus, Pediococcus, Oenococcus, Leuconostoc, Weisella, Carnobacterium*, and *Tetragenococcus. Proprionibacterium* sp., *Bifidobacterium* spp., *Enterococcus* spp., *Corynebacterium glutamicum, Arthrobacter* sp., *Micrococcus luteus* and *Staphylococcus equorum. Geotrichum candidum, Yarrowia lipolytica, Kluyveromyces lactis, Debaryomyces hansenii, Saccharomyces cerevisiae.*

Host cells may be transfected with the nucleotide sequences, or functional equivalent thereof, transiently or stably, as is well known in the art.

Any known method for introducing nucleotide sequences into host cells may be used. It is only necessary that the particular genetic engineering procedure used be capable of successfully introducing the desired nucleotide sequences, or functional equivalents thereof, into the host cell capable of expressing the desired amino acid sequences, or functional equivalents thereof. These methods may involve introducing cloned genomic DNA, cDNA, synthetic DNA or other foreign genetic material into a host cell and include the use of calcium phosphate transfection, polybrene, protoplast fusion, electroporation, liposomes, microinjection, expression vectors, and the like.

Expression vectors, both as individual expression vectors or as libraries of expression vectors, comprising at least one nucleic acid sequences disclosed in SEQ. ID. Nos. 1, 3, 5, and 7, or functional equivalent thereof, may be introduced and expressed in a cell's genome, a cell's cytoplasm, or a cell's nucleus by a variety of conventional techniques.

It is well within the purview of the person skilled in the art to select a suitable technique.

According to an illustrative embodiment, expression vectors may be used to transfect host cells with the nucleic acid sequences disclosed in SEQ. ID. Nos. 1, 3, 5, and 7, or functional equivalents thereof.

In another aspect of the present invention there is provided a vector comprising at least one nucleotide sequence disclosed in SEQ. ID. Nos. 1, 3, 5, and 7, or functional equivalent thereof.

Any suitable expression vector may be used. Non limiting examples of types of vectors include bacteriophage, plasmid, or cosmid DNA expression vectors; viral expression vectors, or bacterial expression vectors.

It is well within the purview of the person skilled in the art to select a suitable expression vector depending on the host cells in question and the desired effect.

In an illustrative embodiment the vector is selected from pBL, pET-22b(+), Pgem-5z, pGIV1.

After transfection, the transfected cells may be cultured using standard culturing conditions well known in the art.

It will be apparent to the skilled person that different cells require different culture conditions including appropriate temperature and cell culture media. It is well within the purview of the person skilled in the art to decide upon culture conditions depending on the cells in question and the desired end result.

In another aspect, there is provided a method of producing an enzyme with thioesterase activity comprising one or more of the amino acid sequences, or functional equivalents thereof, disclosed in SEQ. ID. Nos. 2, 4, 6, and 8, comprising inserting a nucleotide sequence comprising at least one nucleotide sequence disclosed in SEQ. ID. Nos. 1, 3, 5, and 7, or functional equivalent thereof, into a vector; transforming a host cell with the vector and growing the transformed host cell in a suitable culture medium.

As stated above, it will be apparent to the skilled person that different cells require different culture conditions including appropriate temperature and cell culture media. It is well within the purview of the person skilled in the art to decide upon culture conditions depending on the cells in question and the desired end result.

In a particular illustrative embodiment the cells used were *Brevibacterium, Cornynebacterium* or *E Coli* cells and the culture medium was dairy or whey based.

In another particular illustrative embodiment the cells used were *Brevibacterium, Cornynebacterium* or *E Coli* cells and the culture medium was selected from tripticase-soy, de Man-Rogosa-Sharpe (MRS), Elliker's, M17, nutrient broth or LB medium. Cells were incubated overnight at 37° C.

In order to increase the yield of the thioesterase enzymes, the nucleotide sequences disclosed in SEQ. ID. Nos. 1, 3, 5, and 7, or functional equivalents thereof, may be over expressed by placing them under the control of a strong constitutive promoter.

It is well within the purview of the person skilled in the art to select a suitable constitutive promoter depending on the host cells and vector in question.

If desired the thioesterase enzymes comprising the amino acid sequences disclosed in SEQ. ID. Nos. 2, 4, 6, and 8, or functional equivalents thereof, may be isolated from the culture medium using methods well known in the art.

The isolated thioesterase enzymes comprising at least one of the amino acid sequences disclosed in SEQ. ID. Nos. 2, 4, 6, and 8, or functional equivalent thereof, or the transfected host cells comprising at least one of the nucleotide sequences disclosed in SEQ. ID. Nos. 1, 3, 5 and 7, or functional equivalent thereof, may be used to produce thioesters.

In another aspect there is provided a method of producing thioesters comprising contacting at least one thioesterase enzyme comprising at least one amino acid sequences disclosed in SEQ. ID. Nos. 2, 4, 6, and 8, or functional equivalent thereof, and/or at least one host cells comprising at least one of the nucleotide sequences disclosed in SEQ. ID. Nos. 1, 3, 5 and 7, or functional equivalent thereof, with at least one suitable substrate, incubating the mixture, isolating the crude product containing the thioester and, purifying the crude product to obtain only the thioester.

Incubation may be carried out at a temperature of 20° C. to 40° C., at a pH of 4 to 9, for a time period ranging from 1 to 100 hours.

In an illustrative embodiment incubation is carried out at a temperature of 25° C. to 38° C., at a pH of 6 to 8, for a time period ranging from 1 to 72 hours.

Short chain fatty acid coenzyme A derivatives have been found by the applicant to be suitable substrates for the thioesterase enzymes comprising at least one of the amino acid sequences disclosed in SEQ. ID. Nos. 2, 4, 6, and 8, or functional equivalent thereof.

In an illustrative embodiment the suitable substrate comprises a short chain fatty acid coenzyme A (SCFA-CoA).

In another illustrative embodiment a suitable substrate comprises a C1-C8 SCFA-CoA.

The transfected host cells and/or enzymes of the present invention may be used in mobilised or immobilised form.

In an illustrative embodiment the enzymes and/or host cells are used in immobilised form.

Any purification technique may used to purify the crude product and it is well within the purview of the person skilled in the art to decide on such a technique. Non limiting examples of purification techniques include: affinity purification, centrifugation, chromatography.

In another aspect of present invention there is provided a thioester obtainable or produced by a method as described herein.

In another aspect there is provided a kit for producing thioesters comprising at least one thioesterase enzyme comprising at least one amino acid sequence disclosed in SEQ. ID. Nos. 2, 4, 6, and 8, or functional equivalent thereof, and/or at least one host cells comprising at least one of the nucleotide sequences disclosed in SEQ. ID. Nos. 1, 3, 5 and 7, or functional equivalent thereof, and at least one suitable substrate.

The kit may be used to carry out the method, as herein disclosed, for producing thioesters.

In an illustrative embodiment the suitable substrate comprises a short chain fatty acid coenzyme A (SCFA-CoA).

In another illustrative embodiment the suitable substrate comprises a C1-08 SCFA-CoA.

The C1-08 SCFA-CoA substrate may be provided in a concentration from 0.01 µM-500 µM, 0.01 µM-200 µM, 0.01 µM-50 µM.

It is known that the quantity and ratio of thioesters present in cheese affect its flavour.

The thioesters are produced by microbes present in the cheese during its manufacturing and ripening. These microbes are often added to the cheese as starter cultures.

In another aspect there is provided a method of flavouring cheese comprising adding to a cheese during its manufacture process at least one thioesterase enzyme comprising at least one amino acid sequences disclosed in sequence ID numbers 2, 4, 6, and 8, or functional equivalent thereof, and/or at least one host cells comprising at least one of the nucleotide sequences disclosed in sequence ID numbers 1, 3, 5 and 7, or functional equivalent thereof.

In an illustrative embodiment the thioesterase enzyme(s) and/or host cell(s) are added as part of a starter culture.

In another illustrative embodiment the thioesterase enzyme(s) and/or host cell(s) are added as part of a starter culture added to milk.

In another aspect there is provided a cheese product obtainable by or produced according to the method herein above defined.

The nucleotide sequences disclosed in SEQ. ID. Nos. 1, 3, 5, and 7, or functional equivalents thereof, may be used to screen and identify wild type organisms containing genes encoding the thioesterase enzymes encoded by the amino acid sequences disclosed in SEQ. ID. Nos. 2, 4, 6, and 8, or functional equivalents thereof.

In another aspect there is provided the use of the nucleotide sequences disclosed in SEQ. ID. Nos. 1, 3, 5, and 7, or functional equivalents thereof, as markers in screening methods to screen for wild type organisms capable of producing the thioesterase enzymes encoded by the amino acid sequences disclosed in SEQ. ID. Nos. 2, 4, 6, and 8, or functional equivalents thereof.

In another aspect there is provided a method of identifying organisms capable of producing the thioesterase enzymes encoded by the amino acid sequences disclosed in SEQ. ID. Nos. 2, 4, 6, and 8, or functional equivalents thereof, comprising using the nucleotide sequences disclosed in SEQ. ID. Nos. 1, 3, 5, and 7, or functional equivalents thereof, as markers in screening methods.

The organisms identified in the method may be any prokaryotic and eukaryotic organisms.

In an illustrative embodiment the organisms are wild type organisms.

Any known screening method may be used. Examples of well-known screening methods include, but are not limited to, computer driven nucleotide or protein homology searches of public sequence databases, nucleotide screening via high-throughput sequencing, and polymerase chain reaction (PCR) screening.

The thioesters formed by the methods disclosed herein may be isolated and purified for use as flavouring compounds in many compositions and consumable products.

In another aspect there is provided compositions comprising at least one thioester obtained or produced by the methods herein described.

In another aspect there is provided a method of creating, or modifying the flavour of a composition comprising adding to said composition, at least one thioester formed as disclosed herein.

The thioesters may be present or added into a composition in neat form or in a solvent, or they may first be modified, for example by entrapment with an entrapment material such as for example polymers, capsules, microcapsules, nanocapsules, liposomes, precursors, film formers, absorbents such as for example by using carbon zeolites, cyclic oligosaccharides and mixtures thereof, or they may be chemically bound to a substrates which are adapted to release the thioesters upon application of an exogenous stimulus such as light, enzyme, or the like.

One type of thioester may be the sole flavouring component of a composition. Alternatively, multiple types of thioesters may be used in combination.

The composition may additionally comprise other flavourant ingredients and excipients, for example carrier materials, conventionally used in flavour compositions.

Said other flavourant ingredients include, but are not limited to, natural flavours, artificial flavours, spices, seasonings, and the like. Exemplary flavouring ingredients include synthetic flavour oils and flavouring aromatics and/or oils, oleoresins, essences, distillates, and extracts derived from plants, leaves, flowers, fruits, and so forth, and combinations comprising at least one of the foregoing.

Further examples of other flavourant ingredients can be found in "Chemicals Used in Food Processing", publication 1274, pages 63-258, by the National Academy of Sciences.

Said excipients conventionally used in flavour compositions include, but are not limited to, solvents (including water, alcohol, ethanol, oils, fats, vegetable oil, and miglyol), binders, diluents, disintegranting agents, lubricants, flavouring agents, coloring agents, preservatives, antioxidants, emulsifiers, stabilisers, flavour-enhancers, anti-caking agents, and the like.

Further examples of flavourant ingredients and excipients conventionally used in flavour compositions may be found in "Perfume and Flavour Materials of Natural Origin", S. Arctander, Ed., Elizabeth, N.J., 1960; in "Perfume and Flavour Chemicals", S. Arctander, Ed., Vol. I & II, Allured Publishing Corporation, Carol Stream, USA, 1994; in "Flavourings", E. Ziegler and H. Ziegler (ed.), Wiley-VCH Weinheim, 1998, and "CTFA Cosmetic Ingredient Handbook", J. M. Nikitakis (ed.), 1st ed., The Cosmetic, Toiletry and Fragrance Association, Inc., Washington, 1988.

Other suitable and desirable ingredients of flavour compositions are described in standard texts, such as "Handbook of Industrial Chemical Additives", ed. M. and I. Ash, $2^{nd}$ Ed., (Synapse 2000).

The thioesters formed as disclosed herein may be used in compositions at a concentration of up to 100%. According to certain embodiments, the thioesters may be included in the compositions at a concentration in the range of about 0.01% to about 99%. According to other embodiments, the thioesters may be included in the compositions at a concentration in the range of about 1% to about 99%.

In another aspect there is provided a method of creating, enhancing or modifying the flavour of a consumable product comprising adding to said consumable product at least one thioester formed as disclosed herein.

The thioesters formed as disclosed herein, or compositions containing at least one thioester as disclosed herein, can be added to consumable products by using conventional techniques to directly admix said thioesters or composition into the consumable product.

The quantities in which the thioesters formed as disclosed herein may be added to consumable products may vary within wide limits and depend, inter alia, on the nature of the consumable product, on the effect desired, the purpose of adding the thioesters formed as disclosed herein, to a consumable product, for example enhancing or creating a taste, and on the nature and quantity of any other components comprised in the consumable product, for example other flavour ingredients. It is well within the purview of the person skilled in the art to decide on suitable quantities of the thioesters formed as disclosed herein to incorporate into a consumable product depending on the end use and effect required.

Typical non-limiting concentrations, of the thioesters formed as disclosed herein, in ppm by weight based on the weight of the consumable product, are about 500 ppm to about 0.01 ppm, more particularly about 250 ppm to about 0.01 ppm, still more particularly about 100 ppm to about 1 ppm.

In another aspect there is provided a consumer product comprising at least one thioester obtained or produced by the methods herein described.

The term consumable product(s) as used herein means any product that is intended to be placed in the oral cavity and ingested, or to be used in the mouth and then discarded. Suitable consumable products include, but are not limited to, sauces, condiments, foodstuffs of all kinds, confectionery products, baked products, sweet products, savoury products including meat flavoured and meat products and vegetable flavoured and vegetable products, dairy products, beverages, oral care products and combinations thereof.

Exemplary foodstuffs include, but are not limited to, chilled snacks, sweet and savoury snacks, fruit snacks, chips/crisps, extruded snacks, tortilla/corn chips, popcorn, pretzels, nuts, other sweet and savoury snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, UHT soup, frozen soup, pasta, canned pasta, dried pasta, chilled/fresh pasta, noodles, plain noodles, instant noodles, cups/bowl instant noodles, pouch instant noodles, chilled noodles, snack noodles, dried food, dessert mixes, sauces, dressings and condiments, herbs and spices, spreads, jams and preserves, honey, chocolate spreads, nut-based spreads, and yeast-based spreads.

Exemplary confectionery products include, but are not limited to, chewing gum (which includes sugarised gum, sugar-free gum, functional gum and bubble gum), centerfill confections, chocolate and other chocolate confectionery, medicated confectionery, lozenges, tablets, pastilles, mints, standard mints, power mints, chewy candies, hard candies, boiled candies, breath and other oral care films or strips, candy canes, lollipops, gummies, jellies, fudge, caramel, hard and soft panned goods, toffee, taffy, liquorice, gelatin candies, gum drops, jelly beans, nougats, fondants, combinations of one or more of the above, and edible compositions incorporating one or more of the above.

Exemplary baked products include, but are not limited to, alfajores, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savoury biscuits and crackers, bread substitutes, Exemplary sweet products include, but are not limited to, breakfast cereals, ready-to-eat ("rte") cereals, family breakfast cereals, flakes, muesli, other rte cereals, children's breakfast cereals, hot cereals, Exemplary savoury products include, but are not limited to, salty snacks (potato chips, crisps, nuts, tortilla-tostada, pretzels, cheese snacks, corn snacks, potato-snacks, ready-to-eat popcorn, microwaveable popcorn, pork rinds, nuts, crackers, cracker snacks, breakfast cereals, meats, aspic, cured meats (ham, bacon), luncheon/breakfast meats (hotdogs, cold cuts, sausage), tomato products, margarine, peanut butter, soup (clear, canned, cream, instant, UHT), canned vegetables, pasta sauces.

Exemplary dairy products include, but are not limited to, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/UHT milk, full fat long life/UHT milk, semi skimmed long life/UHT milk, fat-free long life/UHT milk, goat milk, condensed/evaporated milk, plain condensed/evaporated milk, flavoured, functional and other condensed milk, flavoured milk drinks, dairy only flavoured milk drinks, flavoured milk drinks with fruit juice, soy milk, sour milk drinks, fermented dairy drinks, coffee whiteners, powder milk, flavoured powder milk drinks, cream, yoghurt, plain/natural yoghurt, flavoured yoghurt, fruited yoghurt, probiotic yoghurt, drinking yoghurt, regular drinking yoghurt, probiotic drinking yoghurt, chilled and shelf-stable desserts, dairy-based desserts, soy-based desserts, Exemplary beverages include, but are not limited to, flavoured water, soft drinks, fruit drinks, coffee-based drinks, tea-based drinks, juice-based drinks (includes fruit and vegetable), milk-based drinks, gel drinks, carbonated or non-carbonated drinks, powdered drinks, alcoholic or non-alcoholic drinks.

Thioesters are particularly important flavouring ingredients for dairy products, particularly cheese flavoured products. In particular, the thioester MTB, preferably used in combination with MTA and/or MTP, is desired for providing an authentic cheese flavor with good flavor impact.

In an illustrative embodiment the consumable product, comprising at least one thioester formed as disclosed herein, is a cheese flavoured product.

In another illustrative embodiment the consumable product is a cheese flavoured product comprising MTA, and/or MTB, and/or MTP formed as disclosed herein.

Sequence Identification

The invention has been described with reference to the following sequence ID numbers:

SEQ ID No. 1—Depicts a nucleotide sequence encoding the thioesterase enzyme 425.

SEQ ID No. 2—Depicts an amino acid sequence of the thioesterase enzyme 425.

SEQ ID No. 3—Depicts a nucleotide sequence encoding one of the thioesterase 1875.

SEQ ID No. 4—Depicts an amino acid sequence of the thioesterase enzyme 1875.

SEQ ID No. 5—Depicts a nucleotide sequence encoding the thioesterase enzyme 3320.

SEQ ID No. 6—Depicts an amino acid sequence of the thioesterase enzyme 3320.

SEQ ID No. 7—Depicts a nucleotide sequence encoding the thioesterase enzyme 1874.

SEQ ID No. 8—Depicts an amino acid sequence of the thioesterase enzyme 1874.

The following examples are set forth to describe the invention further detail and to illustrate the disclosed methods and products. However, the examples should not be construed as limiting in any manner.

EXAMPLES

Example 1—Thioesterase Gene Cloning for Protein Expression

DNA sequences of thioesterase enzymes (hereinafter TE) TE 0425, TE 1875, TE 3320, and TE 1874 were obtained from B. linens strain ATCC9174 by amplification using polymerase chain reaction (PCR) with gene-specific primers (Table 1).

The primers include restriction sites to allow directional cloning of the gene in the pET-22b(+) vector (Novagen), while avoiding sites that occur within the genes to be cloned. The 5' primers include an XbaI site followed by the sequence AGGAGGATTAACATATG (SEQ ID NO: 9), which provides a strong E. coli ribosome binding site and ATG start codon. After the ATG codon each 5' primer includes an in-frame gene-specific sequence of 14-20 bases starting with the first base of the second codon of the open reading frame encoding the specific protein.

The 3' primers includes a SalI or XhoI site and a gene-specific sequence corresponding to the 17-23 base 3' sequence of the specific open reading frame except for the native stop codon.

The pET-22b(+) vector is designed by Novagen to provide both inducible expression in E. coli and protein purification by the binding to nickel columns of a polyhistidine domain incorporated into the expressed protein. Transcription of genes cloned into this vector is designed to require the addition of the inducer IPTG, and use of the pET-22b(+) vector system for the purposes outlined in this invention was performed in full accordance to the manufacturers recommendations.

For gene expression, E. coli BL21(DE3) host cells, which express the T7 RNA polymerase required for the employed pET-22b(+) vector, were used.

Cloning of the resulting gene-specific XbaI to SalI or XhoI fragments into the pET-22b(+) vector generated open reading frames with an in-frame sequence encoding a C-terminal His tag domain and a stop codon from the vector backbone.

TABLE 1

Gene-specific primers used to clone TE genes into the pET-22b(+) vector

| Gene | 5' Site | 3' Site | Primers Used[1] |
|---|---|---|---|
| TE 0425 | XbaI | | GAATTCTAGAAGGAGGATTAACATATGTCCGTGAA GACATTCGAG (SEQ ID NO: 10) |
| | | SalI | AGATCTGTCGACGCCGGCCTCGGCGCCGTATTC (SEQ ID NO: 11) |
| TE 1875 | XbaI | | CAATTGTCTAGAAGGAGGATTAACATATGTGTTCA CGATCCTATCGCGG (SEQ ID NO: 12) |
| | | XhoI | AGATCTCTCGAGTCGGTTGCGACCCCGCATCGGT (SEQ ID NO: 13) |
| TE 3320 | XbaI | | GAATTCTCTAGAAGGAGGATTAACATATGAATCCG CAGTCGGACGCA (SEQ ID NO: 14) |
| | | XhoI | AGATCTCTCGAGGTTGGCCTCCTTCGGCATGGGG A (SEQ ID NO: 15) |

TABLE 1-continued

Gene-specific primers used to clone TE genes
into the pET-22b(+) vector

| Gene | 5' Site | 3' Site | Primers Used[1] |
|---|---|---|---|
| TE 1874 | XbaI | | GAATTCTAGAAGGAGGATTAACATATGAGCGATGC AGAACCCACAG (SEQ ID NO: 16) |
| | | XhoI | AGATCTCTCGAGCTGCGGAGCCTTCACACGGAC (SEQ ID NO: 17) |

Following polymerase chain reaction (PCR) amplification of the thioesterase genes with a mixture of the proofreading Pwo and Taq polymerases (Expand 20 kb$^{plus}$ PCR System, Roche Diagnostics GmbH), the PCR products were cloned without restriction digestion into the pGEM-5Z vector, using a pGEMT Vector System I cloning kit (Promega Corporation).

After ligation to the vector DNA and electroporation, *E. coli* DH5α transformant clones with the putative gene inserts were selected on LB agar plates containing 50 µg/mL ampicillin. The pGEM-5Z cloning allowed an initial screening of clones for inserts using the blue/white β-galactosidase gene inactivation screen. Transformants were then screened for appropriately-sized plasmids by electrophoresis on 0.8% agaraose gels of plasmid DNA recovered from the ampicillin resistant colonies.

In an alternative method to the above, the PCR products were cloned directly into pET-22b(+) after restriction digestion at the 5' and 3' restriction sites included in the PCR primer sequences.

Plasmid DNAs from selected colonies were then digested with restriction enzymes to confirm the presence of insert DNA with the predicted restriction sites flanking the inserts and sizes using agarose gel electrophoresis of the digestion products. Inserts passing these screens were sequenced using primers binding to vector sites flanking the inserts. These were the SP6 and T7 promoter primers for pGEM-5Z clones and the T7 promoter and T7 terminator primers for the pET-22b(+) clones.

Sequencing was done using big dye terminator methodology. Clones with the expected sequences were identified in each case by perfect computer-based homology matches to their respective gene in the *B. linens* strain ATCC 9174 genome sequence.

For the sequences cloned initially in the pGEM-5Z vector, the inserts were recovered from appropriate restriction digestions by elution from preparative agarose gels and then transferred into pET-22b(+) and screened as described above. After obtaining the expected pET-22b(+) constructs in *E coli* DH5a cells, the plasmids were recovered and transformed by electroporation into *E. coli* BL21(DE3) cells for protein expression.

Example 2—Purification of the Cloned Thioesterases

Protein expression was induced in the *E. coli* BL21 (DE3) cells prepared in example 1 through the addition of 0.5 mM of IPTG to batch cultures (100 to 250 mL) comprising the aforementioned *E. coli* cells.

The *E. coli* cells were then incubated for 2-4 h, after which time purification of the His-tagged proteins was performed under native conditions using the nickel-charged resin sold under the trade name Ni-NTA agarose (Invitrogen).

The incubated *E. coli* cells were then added to a solution comprising 50 mM of Na-phosphate (pH 8.0), 20 mM of imidazole, 0.5 M of NaCl buffer, and disrupted by vortexing with glass beads.

The solution comprising the disrupted cells was then added to a purification column comprising 1.5 ml of NI-NTA agrose resin, prepared as directed by the manufacturer.

The cloned thioesterase proteins were extracted from the purification column with a buffer containing 50 mM of imidazole. After extraction the proteins were further eluted with 250 mM of the same buffer.

The extracted proteins were then dialyzed against 50 mM TrisHCl buffer (pH 8.0) at 4° C. The buffer was changed 4 times throughout the process.

Each thioesterase protein was then concentrated using 3K Amicon Ultra-4 cartridges (Millipore, Inc., Billerica, Mass.) employed as directed by the manufacturer.

The concentrations of each of the individual thioesterase proteins were determined using a micro-Lowry kit employed as directed by the kit supplier (Sigma).

Example 3—SFCA's as Substrate

The ability of purified TE 425, TE 3320, TE 1875, and TE 1874 to produce thioesters from fatty acids was determined. Unless stated otherwise the term solution should be interpreted as being a water based solution.

A short chain fatty acid (hereinafter SCFA) mixture containing 10 mM of each of formic acid ($C_1$), acetic acid ($C_2$), propionic acid ($C_3$), butyric acid and iso-butyric acid ($C_4$), valeric acid and iso-valeric acid ($C_5$) and hexanoic acid ($C_6$) was prepared. This mixture was then diluted to yield a solution with a final total $C_1$ to $C_6$ SCFA concentration of 80 µM.

The TE 425, TE 3320, TE 1875 and TE 1874 proteins purified as described in example 2 were each separately diluted to yield separate solutions with final enzyme concentrations of 0.35 µM.

Four sample solutions comprising 100 mM of phosphate buffer (pH 7.2), 100 µM of bovine serum albumin (hereinafter BSA), 25 µM of methanethiol (hereinafter MeSH), 25 µM of coenzyme A (hereinafter CoASH), 2.5 µM of a composition containing equal amounts of pyridoxal-phosphate, pyridoxamine and pyridoxal (hereinafter pyridoxal cocktail), 80 µM of the (C1-C6) SCFA mix prepared above, 10 µM of furfuryl alcohol, and 100 µl of one of the four 0.35 µM enzyme solutions, were prepared.

Control samples were also prepared.

Control 1 was a solution comprising 100 mM of phosphate buffer (pH 7.2), 100 µM of BSA, 25 µM of MeSH, 25 µM of CoASH, 2.5 µM of pyridoxal cocktail, 80 µM of the (C1-C6) SCFA mix, and 10 µM of furfuryl alcohol, but no enzyme.

Controls 2-5 were solutions comprising 100 mM of phosphate buffer (pH 7.2), 100 µM of BSA, 25 µM of MeSH, 25 µM of CoASH, 2.5 µM of pyridoxal cocktail, 80 µM of the (C1-C6) SCFA mix, 10 µM of furfuryl alcohol, and 100 µl of one of the four 0.35 µM enzyme solutions, but no (C1-C6) SCFA mix.

The contents of the samples and controls are illustrated in table 2.

TABLE 2

| Samples (1-4) | Control 1 (no enzyme) | Controls 2-5 (no substrate) |
|---|---|---|
| 100 mM of phosphate buffer | 100 mM of phosphate buffer | 100 mM of phosphate buffer |
| 100 μM of BSA | 100 μM of BSA | 100 μM of BSA |
| 25 μM of MeSH | 25 μM of MeSH | 25 uM of MeSH |
| 25 μM of CoASH | 25 μM of CoASH | 25 μM of CoASH |
| 2.5 μM of pyridoxal cocktail | 2.5 μM of pyridoxal cocktail | 2.5 μM of pyridoxal cocktail |
| 80 μM (C1-C6) SCFA mix | 80 μM (C1-C6) SCFA mix | |
| 100 μl of one of the four 0.35 μM enzyme solutions | | 100 μl of one of the four 0.35 μM enzyme solutions |
| 10 μM of furfuryl alcohol | 10 μM of furfuryl alcohol | 10 μM of furfuryl alcohol |

After preparation all samples were then incubated at 37° C. for 35 min, with solid phase microextraction (SPME) carried out at the same time.

The 10 μM of furfuryl alcohol was added to the sample to correct for SPME variability.

For performing the SPME fibers coated with carboxen/polydimethylsiloxane were used. The coating thickness was 85 mμm The analytes absorbed or coated on the SPME fibres were then analysed by gas chromatography and mass spectrometry (GC-MS) at selected time intervals.

None of the enzymes demonstrated thioester synthesis activity under these assay conditions; i.e. no detectable production of methylthioacetate, methylthiopropionate, methylthiobutyrate, and methylthiovalerate was recorded using the SCFA mix as a substrate.

Follow up experiments with single SCFAs as the substrate gave a similar negative outcome.

Example 4—Coenzyme A-SFCAs Derivatives as Substrates

Since thioester synthesis was not detected from SCFA substrates, the ability of purified TE 425, TE 3320, TE 1875, and TE 1874 to catalyze MTB production from butyryl-coenzyme A (hereinafter butyryl-CoA) instead of free butyrate was tested.

Four sample solutions were prepared by adding 5 μM of one of the four thioesterase enzymes into a solution comprising 0.22 mM of BSA, 100 mM of phosphate buffer (pH 8.0), 0.03 mM butyryl-CoA, and 0.03 mM MeSH.

Six control samples were also prepared;

Control 7 was a solution comprising 0.22 mM of BSA, 100 mM of phosphate buffer (pH 8.0), 0.03 mM butyryl-CoA, and 0.03 mM MeSH, but no enzyme.

Controls 8 to 11 were solutions comprising 0.22 mM of BSA, 100 mM of phosphate buffer (pH 8.0), and 5 μM of the four thioesterase enzymes, but no butyryl-CoA.

Control 12 was a solution comprising 40 μM of MTB only. This was used as a control for SPME detection of MTB.

The contents of the samples and controls are illustrated in table 3.

TABLE 3

| Samples 1-6 | Control 7 | Controls 8-11 | Control 12 |
|---|---|---|---|
| 100 mM of phosphate buffer (pH 8.0) | 100 mM of phosphate buffer (pH 8.0) | 100 mM of phosphate buffer (pH 8.0) | |
| 0.22 μM of BSA | 0.22 μM of BSA | 0.22 μM of BSA | |
| 0.03 μM of MeSH | 0.03 μM of MeSH | 0.03 μM of MeSH | |
| 0.03 μM of Butyryl-CoA | 0.03 μM of Butyryl-CoA | | |
| 5 μm of one of the four enzymes (TE425, TE 3320, TE 1875, and TE1874) | | 5 μm of one of the four enzymes (TE425, TE 3320, TE 1875, and TE1874) | |
| | | | 40 μM MTB |

After preparation all samples were incubated at 32° C. After 2 hrs of incubation SPME was carried out for 30 mins with the temperature kept at 32° C. throughout the procedure. This resulted in a total incubation time of 2.5 hrs.

10 μM of furfuryl alcohol was added to the sample to correct for SPME variability.

For performing the SPME fibers coated with carboxen/polydimethylsiloxane were used. The coating thickness was 85 μm.

The analytes absorbed or coated on the SPME fibres were analysed using GC-MS at selected time intervals. Results from this analysis are shown in table 4.

TABLE 4

MTB production from butyryl-CoA and MeSH by TE enzymes

| | m/z 118 peak area | Concentration of MTB (μM) |
|---|---|---|
| Control 7 | 0 | 0 |
| Controls 8-11 | 0 | 0 |
| Control 12 | 62.02 | 40 |
| Sample 1 TE425 | 2.96 | 1.908 |
| Sample 2 TE 1874 | 1.56 | 1.006 |
| Sample 3 TE 3320 | 11.73 | 7.57 |
| Sample 4 TE 1875 | 6.15 | 3.966 |

Control 12 only contained MTB. This control indicated the expected m/z ratio for MTB is 118.

Controls 7 to 12 did not show a peak at 118 and consequently it can be assumed that these samples do not contain any MTB (Table 3)

Samples 1, 2, 3, and 4 all show peaks at 118. This proves that in each case MTB has been formed and consequently that TE 425, TE 3320, TE 1875, and TE 1874 are thioesterase enzymes capable of producing thioesters from CoA-SCFA derivatives.

The amount of MTB produced by each enzyme can be estimated from the M/Z 118 corresponding GC peak area that should be roughly proportional to the amount of MTB in the sample. All peak areas and corresponding MTB concentrations are listed in table 4.

Example 5—TE Enzymes Substrate Preferences and Product Profiles

The ability of purified TE 425 and TE 3320 to catalyze thioester production from a mixture of SCFA CoA-derivatives was determined.

To investigate this activity, CoA-SFCA's were synthesized in a two step reaction.

A preparation of fatty acid anhydrides was made via the following method:

10 mmoles of N,N'-dicyclohexylcarbodiimide (DCC) was added to 50 mL of dry carbon tetrachloride ($CCl_4$) (50 mL). This solution was then added to a second solution containing 20 mmoles of the SCFA mix in 150 mL of dry $CCl_4$.

The reaction mixture was kept at room temperature for 5 hrs after which time the dicyclohexylurea (DCU) precipitate was removed by filtration. Any $CCL_4$ in the precipitate was removed by evaporation under reduced pressure. The solid residue was re-crystallised from acetone. The crystals were washed with $CCL_4$ to remove traces of chemicals. The products were then separated by chromatography to yield pure $C_2$ to $C_8$ SCFA anhydrides.

After the SCFA anhydrides had been prepared and separated 30 μm of each of the $C_2$ to $C_8$ SCFA anhydrides was added to a separate solution of 45 μmol of 2.5 μM of pyridoxal cocktail in 30 mL of ice cold water.

Sodium bicarbonate was added to all the samples to ensure that in each case the pH was 7-7.5. All the mixtures were kept in an ice-bath and shaken frequently for 60 min.

The $C_2$ to $C_8$ SCFA-CoA's were purified by precipitation with trichloroactetate (hereinafter TCA) and re-suspended in the water enzyme activity assay.

Once the SCFA CoA's had been formed, samples comprising different thioesterase and SFCA-CoA's were prepared by adding 35 μM of one of the thioesterase enzymes, either TE 425 or TE3320, plus 120 μM of the $C_2$ to $C_8$ SCFA-CoA mixture into a solution containing 100 μM of BSA, 100 mM of phosphate buffer (pH 7.2), 25 μM of MeSH, and 2.5 μM of pyridoxal cocktail.

Control samples were also prepared;

Control 13 was a solution comprising 120 μM of the $C_2$ to $C_8$ SCFA-CoA mixture, 100 μM of BSA, 100 mM of phosphate buffer (pH 7.2), 25 μM of methanethiol, and 2.5 μM of pyridoxal cocktail, but no enzyme.

Controls 14 to 15 were solutions comprising 35 μM of one of the thioesterase enzymes, either TE 425 or TE3320, 100 μM of BSA, 100 mM of phosphate buffer (pH 7.2), 25 μM of methanethiol, and 2.5 μM of pyridoxal cocktail, but no $C_2$ to $C_8$ SCFA-CoA mixture.

The contents of the samples and controls are illustrated in table 5.

TABLE 5

| Samples 1-2 | Controls 13 | Controls 14-15 |
| --- | --- | --- |
| 120 μM of the $C_2$ to $C_8$ SCFA-CoA | 120 μM of the $C_2$ to $C_8$ SCFA-CoA | |
| 100 μM of BSA | 100 μM of BSA | 100 μM of BSA |
| 25 μM of MeSH | 25 μM of MeSH | 25 μM of MeSH |
| 100 mM of phosphate buffer (pH 7.2), | 100 mM of phosphate buffer (pH 7.2), | 100 mM of phosphate buffer (pH 7.2), |
| 2.5 μM of pyridoxal cocktail | 2.5 μM of pyridoxal cocktail | 2.5 μM of pyridoxal cocktail |
| 35 μM of one of the thioesterase enzymes, either TE 425 or TE3320 | | 35 μM of one of the thioesterase enzymes, either TE 425 or TE3320 |

All samples were incubated at 37° C. for 35 min, then SPME was carried out for 30 mins with fibers coated (thickness=85 um) with carboxen/polydimethylsiloxane. This resulted in a total incubation time of 45 min.

10 μM of furfuryl alcohol was added to the sample to correct for SPME variability.

Analytes absorbed or coated on the SPME fibres were analysed by GC-MS at selected time intervals.

The results after incubation with equimolar mixture of SCFA-CoA derivatives, shown in table 6, confirm that TE 425 and 3320 have different substrate selectivity.

TE 3320 showed a peak of activity for MTB and MTV formation (C4, C5); suggesting butyryl- and valeryl-CoA are preferred substrates. In contrast, TE 425 gave a slight peak at MTH formation, suggesting hexanoyl-CoA (C6) may be its primary substrate.

TABLE 6

Enzymatic activity of TE 3320 and TE 425 with $C_2$ to $C_8$ SCFA-CoA mixture as substrates

| Thioester Product* | Enzyme activity (by initial velocity method) | | | |
| --- | --- | --- | --- | --- |
| | MTA | MTP | MTB | MTV |
| Control 13 (no enzyme) | 0.0 ± 0.0 | 0.0 ± 0.0 | 0.0 ± 0.0 | 0.0 ± 0.0 |
| Controls 14-15 (no substrates) | 0.2 ± 0.11 | 0.3 ± 0.15 | 0.2 ± 0.12 | 0.2 ± 0.12 |

TABLE 6-continued

Enzymatic activity of TE 3320 and TE 425 with $C_2$ to $C_8$ SCFA-CoA mixture as substrates

| TE 3320 | 0.2 ± 0.11 | 0.1 ± 0.22 | 0.05 ± 0.05 | 0.1 ± 0.04 |
| TE 425 | 0.2 ± 0.04 | 0.1 ± 0.06 | 0.12 ± 0.04 | 0.08 ± 0.05 |

| Thioester Product* | MTH | MTO |
| --- | --- | --- |
| Control 13 (no enzyme) | 0.0 ± 0.0 | 0.0 ± 0.0 |
| Controls 14-15 (no substrates) | 0.1 ± 0.06 | 0.1 ± 0.03 |
| TE 3320 | 0.1 ± 0.05 | 0.1 ± 0.05 |
| TE 425 | 0.1 ± 0.06 | 0.06 ± 0.02 |

*MTA, methylthioacetate; MTP, methylthiopropionate; MTB, methylthiobutyrate; MTV, methylthiovalerate; MTH, methylthiohexanoate; MTO, methylthiooctanoate

Example 6—Production of Various Thioesters by TE3320

A test sample was prepared by adding 100 μL of a solution comprising 0.35 μM of TE 3320 to a solution comprising 100 mM of phosphate buffer (pH 7.2), 100 μM of BSA, 25 μM of methanethiol, 2.5 μM pyridoxal cocktail, and 4.16 μM of each of Acetyl-CoA (C2), Propionyl-CoA (C3), butyryl-CoA (C4), valeryl-CoA (C5), Hexanoyl-CoA (C6), and Octanoyl-CoA (C8).

Two control samples were also prepared.

Control 16 was a solution comprising 100 mM of phosphate buffer (pH 7.2), 100 μM of BSA, 25 μM of methanethiol, 2.5 uM of pyridoxal cocktail, and 4.16 uM of each of Acetyl-CoA C2, Propionyl-CoA C3, butyryl-CoA C4, valeryl-CoA C5, Hexanoyl-CoA C6, and Octanoyl-CoA C8; but no enzyme.

Control 17 was a solution comprising 100 μL of a solution comprising 0.35 μM of TE 3320, 100 mM of phosphate buffer (pH 7.2), 100 μM of BSA, 25 μM of methanethiol, and 2.5 μM of pyridoxal cocktail; but no CoA-SFCA derivatives.

The contents of the samples and controls are illustrated in table 7.

TABLE 7

| Sample | Control 16 | Control 17 |
| --- | --- | --- |
| 100 mM of phosphate buffer (pH 7.2) | 100 mM of phosphate buffer (pH 7.2) | 100 mM of phosphate buffer (pH 7.2) |
| 100 μM of BSA | 100 μM of BSA | 100 μM of BSA |
| 25 μM of methanethiol | 25 μM of methanethiol | 25 μM of methanethiol |
| 2.5 μM of pyridoxal cocktail | 2.5 μM of pyridoxal cocktail | 2.5 μM of pyridoxal cocktail |
| 4.16 uM of each of Acetyl-CoA C2, Propionyl-CoA C3, butyryl-CoA C4, valeryl-CoA C5, Hexanoyl-CoA C6, and Octanoyl-CoA C8 | 4.16 uM of each of Acetyl-CoA C2, Propionyl-CoA C3, butyryl-CoA C4, valeryl-CoA C5, Hexanoyl-CoA C6, and Octanoyl-CoA C8 | |
| 0.35 μM of TE 3320 | | 0.35 μM of TE 3320 |

The samples were then incubated at 32° C. After 2 hrs of incubation SPME was carried out. The SPME took 30 mins and the temperature was kept at 32° C. throughout the procedure. This resulted in a total incubation time of 2.5 hrs.

10 μM of furfuryl alcohol was added to the sample to correct for SPME variability.

For performing the SPME fibers coated with carboxen/polydimethylsiloxane were used. The coating thickness was 85 μm.

The analytes absorbed or coated on the SPME fibres were then analysed using GC-MS.

The results from the GC-MS analysis are shown in table 8.

TABLE 8

Retention times, m/z fragment selection and TE 3320 enzymatic activity of thioester formation.

| Thioester products | Sample TE 3320 Peak Area | Control 16 (No enzyme) | Control 17 (No substrate) |
| --- | --- | --- | --- |
| MTA (C2) 90 m/z/7.9 min | 1.3 | 0 | 0 |
| MTP (C3) 104 m/z/8.6 min | 3.5 | 0 | 0 |
| MTB (C4) 118 m/z/118; 9.3 min | 4.7 | 0 | 0 |
| Methylthiovalerate (C5) 132 m/z/10.2 min | 5.1 | 0 | 0 |
| Methythiohexanoate (C6) 146 m/z/11.12 min | 3.2 | 0 | 0 |
| Methylthiooctanoate (C8) 174 m/z/13.32 min | 3.4 | 0 | 0 |

Controls 16 and 17 both did not show peaks corresponding to any thioester products (Table 8). The sample containing the TE3320 enzyme showed peaks at 7.9, 8.6, 9.3, 10.2, 11.12, and 13.32 mins with m/z values of 90, 104, 118, 132, 146, and 174, respectively.

This result proves that the thioesters were formed and that TE3320 is a thioesterases capable of forming various thioesters from appropriate substrates.

The amount of each thioester produced by TE3320 can be estimated from the corresponding GC peak areas. Each peak corresponds to a particular thioester and the area of each peak should be roughly proportional to the amount of each corresponding thioester in the sample. All peak areas are listed in table 8.

The larger peak area sizes at 9.3 and 10.2 min with m/z values of 118 and 132, respectively, may indicate that TE3320 has a preference for C4 and C5 substrates.

Example 7—Over Expression of B. linens Thioesterases

Over-expression of TE 425, TE 3320, TE 1875 and TE1874 in B. linens or other species of corynebacteria may be achieved via increased gene copy number by inserting a nucleotide sequence of the present invention into a suitable plasmid vector and transforming a host cell with said vector.

Suitable vectors include pGIV1, which is derived from the native plasmid pBLIN1 found in strain *B. linens* ATCC 9174. Features of pGIV1 include the pBLIN1 replication origin and adjoining rep genes, the pUC origin for replication in *E. coli*, a replaceable ampicillin resistance gene flanked by multiple cloning sites where promoter-gene constructs can be inserted, and a gene for kanamycin resistance to facilitate selection in *B. linens* host cells.

Promoter-gene constructs for TE 425, 3320, 1875 and 1874 are comprised of a suitable 5' untranslated region, with operators or promoter motifs that influence the efficiency of transcription or translation, plus the TE coding sequence.

Examples of suitable 5' untranslated ("promoter") regions include the 200 bp region immediately upstream of REBL2645, a gene encoding acetolactate synthase large subunit, which may be strongly upregulated by Met addition, as well as the 200 bp region immediately upstream of RBLE02060, a gene encoding methionyl aminopeptidase that may be constitutively expressed (Cholet et al. 2007, Appl. Microbiol. Biotechnol, 74:1320-1332).

Promoter-gene constructs were assembled following the general PCR strategy described in example 1. The promoter fragments are 200 base pairs in length and flanked on their 5' end by NotI sites and on their 3' end by Eco31I sites. In addition, the 3' promoter primers were constructed to include an ATG start codon, a strong ribosome binding site (AGGAGG) starting ten nucleotides upstream of the start codon, and the 'consensus' sequence CCAC between the ribosome binding site and the start codon. The AGGAGG hexamer is complementary to a region near the 3' end of the *B. linens* 16 S ribosomal RNA sequence.

Thioesterase gene fragments are 603 base pairs for the TE 1875 and 435 base pairs for TE 3320. Both are flanked on their 5' ends by Eco31I sites and on their 3' ends by HindIII sites. The 3' end of the thioesterase gene fragment includes the TGA stop codon immediately 5' to the HindIII site.

These fragments were digested with the appropriate pairs of restriction enzymes and then ligated in triple ligations into pBluescript (Stratagene, Agilent Technologies, Inc., Santa Clara, Calif.) that had been digested with NotI and HindIII. The RBLE02060 and REBL2645 promoter fragments were ligated with the TE 1875 and TE 3320 gene insert fragments in the four pair wise promoter-gene combinations and transformed into *E. coli* DH5 alpha cells.

The presence of correctly assembled promoter-gene combinations in plasmid DNA from prospective clones was confirmed by DNA sequence analysis (Table 9).

After sequence confirmation the insert fragments were recovered as NotI-HindIII restriction fragments for transfer into the *B. linens* shuttle vector pGIV1. The vector was digested in the polylinker region with the NotI and HindIII enzymes, then individual promoter-gene inserts were ligated into the vector and transformed into *E. coli* DH5 alpha cells.

The presence of cloned promoter-gene combinations in recombinant plasmid DNA (pGIV1: TE plasmids) from prospective transformants was confirmed by DNA sequence analysis. Plasmid DNA was then isolated and transformed into *B. linens* ATCC 19391 using the protocol described by Leret et al. 1998 (Microbiol. 144:2827-2836) which is incorporated herein by reference.

Representative isolates of *B. linens* ATCC 19391 transformed with pGIV1: TE plasmids were selected, and overexpression of TE 425, 3320, 1875 or 1874 may be confirmed by real-time quantitative PCR (Q-PCR) of TE mRNA transcripts using primers based on the sequences provided in Table 1. It is well within the purview of the person skilled in the art to design appropriate Q-PCR primers from such sequences and quantify cognate mRNA transcripts.

TABLE 9

Nucleotide sequences for combined promoters and TE gene constructs. Modified ribosome binding site and start codon regions are underlined and in bold font.

| promoters and TE gene constructs | Nucleotide sequences |
|---|---|
| RBLE02060 promoter and TE 1875: | CAGGCTCACCACGTCGCTGAGTCCGGAGAATTCGGGACCGGTCAC ATCTGCCCGTTCGCTCATCACTCCCCTTTGCTCAACATTGTGGCCT TCGCTGGCCGTTCCTTTCACTCTATTATCCTCTCCCACGGCAGGCC CGCACCGACAGGCACCGCAATTGTGGAATATCTGGGTTCAACCGC TCTAGAATAGGAGGCACCATGTGTTCACGATCCTATCGCGGCCCT CACTGCAGCGGTGAAGGTGGCATGATGGGACATATGCACAACCGC ACCACGAATCCCCATCTGAACGAATTCACACGAGTCCTGTTGGAAC TGAGATGGGGAGACATGGATGCCTATGGCCACGTCAACAATGTCA CCCAGCTGCGTCTGCTCGAAGAGGCACGCGTCCGCGCTCTGGGCT CACCGACGCACAGCACCGATGCACCCACAACTCCAGGTCAGCTGG GAATCTCAGGCACGGTATCGGGGATCACAATTCCGGCGATCTTCG CCGAGGCTTCGAACACCACCGAGCTGCTCGTCGCCTCCCACGCGA TCGAATATCGCCGTCCCATTCCCTACCGTGCAGGTCCCATTGCCAT CGATCTCGTCATCAGCGAGGTCAAACCGGCCTCTGTGACGATCGG TTACAGCATCGCCGAACCCGATGGTTCGGTCGGCTATACGCTGGC AGAGACGGTCATCGTCTTTGTAGACAGGACGACCTCCCGACCGCG TCGCCTGACCCAGGAGGAGACAGCAGCAATGGAAGACGTCATTCG ACCTGCCGTACCGATGCGGGGTCGCAACCGATGA (SEQ ID NO: 18) |
| RBLE2645 promoter and TE 1875: | GTCTCCCGTCTGATCGCCGGCAGCAACGAGATCCAGGAGATCGAG ATCAACCCGGTGCGCGTGACCCCGGATGGGGCATTGGCCGTCGA CGCGCTCGTCGTCACGAACCGAGACGACAACGATGGCAGCACCGA CAACGACAGCGGCAGCGACAACCCCGACAACGACAGCAGCACCG ACAACCCCGACAAGGAGGCACCATGTGTTCACGATCCTATCGCGG CCCTCACTGCAGCGGTGAAGGTGGCATGATGGGACATATGCACAA CCGCACCACGAATCCCCATCTGAACGAATTCACACGAGTCCTGTTG GAACTGAGATGGGGAGACATGGATGCCTATGGCCACGTCAACAAT |

TABLE 9-continued

Nucleotide sequences for combined promoters and TE gene constructs. Modified ribosome binding site and start codon regions are underlined and in bold font.

| promoters and TE gene constructs | Nucleotide sequences |
|---|---|
| | GTCACCCAGCTGCGTCTGCTCGAAGAGGCACGCGTCCGCGCTCTG<br>GGCTCACCGACGCACAGCACCGATGCACCCACAACTCCAGGTCAG<br>CTGGGAATCTCAGGCACGGTATCGGGGATCACAATTCCGGCGATC<br>TTCGCCGAGGCTTCGAACACCACCGAGCTGCTCGTCGCCTCCCAC<br>GCGATCGAATATCGCCGTCCCATTCCCTACCGTGCAGGTCCCATTG<br>CCATCGATCTCGTCATCAGCGAGGTCAAACCGGCCTCTGTGACGAT<br>CGGTTACAGCATCGCCGAACCCGATGGTTCGGTCGGCTATACGCT<br>GGCAGAGACGGTCATCGTCTTTGTAGACAGGACGACCTCCCGACC<br>GCGTCGCCTGACCCAGGAGGAGACAGCAGCAATGGAAGACGTCAT<br>TCGACCTGCCGTACCGATGCGGGGTCGCAACCGATGA<br>(SEQ ID NO: 19) |
| RBLE2060 promoter and TE 3320: | CAGGCTCACCACGTCGCTGAGTCCGGAGAATTCGGGACCGGTCAC<br>ATCTGCCCGTTCGCTCATCACTCCCCTTTGCTCAACATTGTGGCCT<br>TCGCTGGCCGTTCCTTTCACTCTATTATCCTCTCCCACGGCAGGCC<br>CGCACCGACAGGCACCGCAATTGTGGAATATCTGGGTTCAACCGC<br>TCTAGAAAGGAGGCACCATGAATCCGCAGTCGGACGCACTTCCA<br>GATGTCTCACTTGCCTCAGCCAGCAACTTCGTCGCCGCCTCGGGG<br>CTCGTCATCGACGAGGTCACGAACACAAGCGTCCGCGGCCATGCC<br>GATCTGGGCAGCGACCACCACACGCCTTGGGGCGTCGTCCACGG<br>CGGCGTGTACACAACGCTCGTGGAGAGCACGGGAAGCATTGGTGC<br>CAGCCACGCTGTGGGCGAGCGCGGCGAGTTCGCCGTCGGCATCC<br>ACAACGCCACCGACTTTCTGCGCCCGACCGCCGGCGCCCGCGTTG<br>CAGTCGAGGGCACCGCCCTGCATCAGGGCCGGACCCAGCAGCTG<br>TGGGAGGTCATCATCACCGACACCTCATCGGACAAGGTCCTGGCC<br>CGCGGCCAGCTGCGCCTGCAGAACGTCCCCATGCCGAAGGAGGC<br>CAACTGA (SEQ ID NO: 20) |
| RBLE2645 promoter and TE3320: | GTCTCCCGTCTGATCGCCGGCAGCAACGAGATCCAGGAGATCGAG<br>ATCAACCCGGTGCGCGTGACCCCGGATGGGGCATTGGCCGTCGA<br>CGCGCTCGTCGTCACGAACCGAGACGACAACGATGGCAGCACCGA<br>CAACGACAGCGGCAGCGACAACCCCGACAACGACAGCAGCACCG<br>ACAACCCCGACAAGGAGGCACCATGAATCCGCAGTCGGACGCACT<br>TCCAGATGTCTCACTTGCCTCAGCCAGCAACTTCGTCGCCGCCTCG<br>GGGCTCGTCATCGACGAGGTCACGAACACAAGCGTCCGCGGCCAT<br>GCCGATCTGGGCAGCGACCACCACACGCCTTGGGGCGTCGTCCA<br>CGGCGGCGTGTACACAACGCTCGTGGAGAGCACGGGAAGCATTG<br>GTGCCAGCCACGCTGTGGGCGAGCGCGGCGAGTTCGCCGTCGGC<br>ATCCACAACGCCACCGACTTTCTGCGCCCGACCGCCGGCGCCCGC<br>GTTGCAGTCGAGGGCACCGCCCTGCATCAGGGCCGGACCCAGCA<br>GCTGTGGGAGGTCATCATCACCGACACCTCATCGGACAAGGTCCT<br>GGCCCGCGGCCAGCTGCGCCTGCAGAACGTCCCCATGCCGAAGG<br>AGGCCAACTGA (SEQ ID NO: 21) |

Example 8—Heterologous Expression of Thioesterases

Heterologous expression of TE 425, TE 3320, TE 1875 and TE1874 in *Lactobacillus casei* other lactic acid bacteria may be achieved via increased gene copy number by inserting a nucleotide sequence of the present invention into a suitable plasmid vector and transforming a host cell with said vector.

Construction of thioesterase gene construct plasmids (hereinafter TE plasmids) for heterologous expression was performed by PCR following the method described in example 1 except that a suitable vector containing suitable 5' untranslated region for heterologous expression of TE genes must be used.

Suitable vectors are those derived from *Lactobacillus casei* or other lactic acid bacteria and may include, but are not limited to, pHADH, a plasmid containing the cloned dhic gene from *L. casei* ATCC 334. (Broadbent et al. 2004, Appl. Environ. Microbiol. 70:4814-4820).

Suitable 5' untranslated region for heterologous expression in pHADH may be derived by PCR amplification of the putative ribosome binding site and promoter region for dhic in using primers P1 and P2 (Table 10) to obtain a 285 bp XbaI/BglII fragment. The coding regions for TE 3320 or TE 1875 were amplified from *B. linens* ATCC9174 genomic DNA using primers B71 and B72 or B73 and B74, respectively.

These reactions yielded the complete TE3320 coding region on a 456 bp BglII/BamHI fragment, or the complete TE1875 coding region on a 609 bp BglII/BamHI fragment. The start codons were one (TE3320) or two (TE1875) basepairs downstream of the BglII site. No recognition sites for these three restriction enzymes (or SacI, see below) are present in the TE genes or in the dhic promoter region.

TABLE 10

PCR primers used to clone TE genes into the pHADH-derived vector

| Organism | Primer Anneal area | Name | Linker* | Sequence |
|---|---|---|---|---|
| *L. casei* | dhic promoter | P1 | XbaI | GTTATCTAGACGATT TCTTATGGAGAG |

TABLE 10-continued

PCR primers used to clone TE genes into the pHADH-derived vector

| Organism | Primer Anneal area | Name | Linker* | Sequence |
|---|---|---|---|---|
| ATCC 334 | 5' | | | (SEQ ID NO: 22) |
| | dhic promoter 3' | P2 | BglII | GTTTAGATCTCTTCC TTTCCAATTTGTCCA CTCACCAG (SEQ ID NO: 23) |
| B. linens ATCC 9174 | TE3320 5' | B71 | BglII | GTTTAGATCTCATGAATCC GCAGTCGGACGCACTTC CAG (SEQ ID NO: 24) |
| | TE3320 3' | B72 | BamHI | GTTTGGATCCTC GAATCAGTGCCCAT CTCAGTTG (SEQ ID NO: 25) |
| | TE1875 5' | B73 | BglII | GTTTAGATCTGCGTG TGTTCACGATCCTATCG CGG (SEQ ID NO: 26) |
| | TE1875 3' | B74 | BamHI | GTTTGGATCCAGTCA TCGGTTGCGACCC CGCATCGG (SEQ ID NO: 27) |

*Restriction endonuclease target site embedded in primer sequence to facilitate directional cloning.

The PCR fragments are digested with BglII and the promoter is separately ligated to each coding sequence. The ligated DNA samples are recovered and checked by PCR amplification with the primer combinations P1/B72 and P1/B74 (Table 10).

The promoter-TE coding region constructs were then digested with XbaI and BamHI and ligated into pBlueScript that was also digested with XbaI and BamHI and transformed into E. coli DH5 alpha. The presence of correctly assembled promoter-gene combinations in transformants was verified by PCR using primers P1×1372 (TE3320) and P1×1374 (TE1875) and DNA sequence analysis of insert regions from recombinant plasmids.

The recombinant plasmids are digested with SacI and BamHI and the promoter-coding region fragments were separated from the pBlueScript vector. The inserts were ligated into SacI/BamHI digested pHADH, which effectively replaces dhic with the promoter-TE coding region, and transformed into E. coli DH5 alpha.

The presence of correctly assembled promoter-gene combinations in transformants was verified by PCR using primers P1xB72 (TE3320) and P1xB74 (TE1875) and DNA sequence analysis of insert regions from recombinant plasmids.

The recombinant plasmids pTE 3320 and pTE 1875 were recovered from E. coli clones and transformed by electroporation into L. casei ATCC 334 or other lactic acid bacteria.

For L. casei, one of several methods to transform cells begins by inoculating stationary-phase cells at 2% (vol/vol) into 500 mL of MRS broth (Difco, Detroit, Mich., USA) and incubating at 37° C. until the suspension reached an absorbance at 600 nm (A600) of 0.8.

The cells were harvested by centrifugation at 5000×g, washed twice with sterile, distilled water, and suspended in 2.5 mL of ice-cold, sterile 30% polyethylene glycol 1450 (Sigma Chemical Co.). 3 μl of the TE plasmid constructs formed above, are mixed with 100 μl of cell suspension in a 0.2 cm electroporation cuvette and placed on ice for 3 min. An electric pulse is delivered in a Bio-Rad Gene Pulser (Bio-Rad Laboratories, Richmond, Calif., USA) set to the following parameters: 2.5 kV, 25 μF, and 2000. After electroporation, 0.9 mL of warmed (37° C.) MRS broth was added, and the cells were incubated at 37° C. for 2 h. Transformed cells were collected on MRS agar containing 5 μg of ERY (Sigma Chemical Co., St. Louis, Mo., USA) per mL.

The presence of the TE vector in lysates from putative transformants was confirmed by electrophoretic separation in 0.6% agarose gels with Tris acetate buffer (40 mM Tris, 20 mM acetic acid, and 2 mM $Na_2EDTA$, pH 8.1). It is well within the purview of the person skilled in the art to select an appropriate lysis procedure for isolation of plasmid DNA, depending on the host cells in question.

The fidelity of promoter-gene combinations in pTE 3320 and pTE 1875 transformants was verified by PCR using primers P1×1372 (TE3320) and P1×1374 (TE1875) and DNA sequence analysis of insert regions.

Overexpression of TE 425, 3320, 1875 or 1874 was confirmed by real-time quantitative PCR (Q-PCR) of TE mRNA transcripts using primers based on the cognate gene sequences.

Alternatively, TE activity in these hosts can be demonstrated by enzyme assay for cell lysates using the method described in example 4.

While the nucleotide and amino acid sequences encoding thioesterase enzymes, and various methods using and products incorporating the same, have been described in connection with various illustrative embodiments, it is to be understood that other similar embodiments may be used or modifications and additions may be made to the described embodiments for performing the same function disclosed herein without deviating there from. The embodiments described above are not necessarily in the alternative, as various embodiments may be combined to provide the desired characteristics. Therefore, the disclosure should not be limited to any single embodiment, but rather construed in breadth and scope in accordance with the recitation of the appended claims.

The invention claimed is:

1. A method of flavouring cheese comprising adding to a cheese during its manufacture process at least one thioesterase enzyme comprising at least one of the amino acid sequences with at least 90% identity to SEQ ID NOS 2, 4, 6, or 8, and/or at least one isolated transfected host cell comprising at least one of the nucleotide sequences with at least 90% identity to SEQ ID NOS 1, 3, 5 or 7.

2. The method of claim 1, wherein the at least one thioesterase enzyme and/or at least one host cell is added as part of a starter culture.

3. The method of claim 1, wherein the at least one thioesterase enzyme comprises an amino acid sequence with at least 90% identity to SEQ ID NO 2.

4. The method of claim 1, wherein the at least one thioesterase enzyme comprises an amino acid sequence with at least 90% identity to SEQ ID NO 4.

5. The method of claim 1, wherein the at least one thioesterase enzyme comprises an amino acid sequence with at least 90% identity to SEQ ID NO 6.

6. The method of claim 1, wherein the at least one thioesterase enzyme comprises an amino acid sequence with at least 90% identity to SEQ ID NO 8.

7. The method of claim 1, wherein the at least one thioesterase enzyme comprises at least one host cell comprising a nucleotide sequence with at least 90% identity to SEQ ID NO 1.

8. The method of claim 1, wherein the at least one thioesterase enzyme comprises at least one host cell comprising a nucleotide sequence with at least 90% identity to SEQ ID NO 3.

9. The method of claim 1, wherein the at least one thioesterase enzyme comprises at least one host cell comprising a nucleotide sequence with at least 90% identity to SEQ ID NO 5.

10. The method of claim 1, wherein the at least one thioesterase enzyme comprises at least one host cell comprising a nucleotide sequence with at least 90% identity to SEQ ID NO 7.

11. A method of obtaining a flavoured cheese product or a cheese flavoured product comprising adding to a cheese during its manufacture process at least one thioesterase enzyme comprising at least one of the amino acid sequences with at least 90% identity to SEQ ID NOS 2, 4, 6, or 8, and/or at least one isolated transfected host cell comprising at least one of the nucleotide sequences with at least 90% identity to SEQ ID NOS 1, 3, 5 or 7.

12. The method of claim 11, wherein the at least one thioesterase enzyme comprises an amino acid sequence with at least 90% identity to SEQ ID NO 2.

13. The method of claim 11, wherein the at least one thioesterase enzyme comprises an amino acid sequence with at least 90% identity to SEQ ID NO 4.

14. The method of claim 11, wherein the at least one thioesterase enzyme comprises an amino acid sequence with at least 90% identity to SEQ ID NO 6.

15. The method of claim 11, wherein the at least one thioesterase enzyme comprises an amino acid sequence with at least 90% identity to SEQ ID NO 8.

16. The method of claim 11, wherein the at least one thioesterase enzyme comprises at least one host cell comprising a nucleotide sequence with at least 90% identity to SEQ ID NO 1.

17. The method of claim 11, wherein the at least one thioesterase enzyme comprises at least one host cell comprising a nucleotide sequence with at least 90% identity to SEQ ID NO 3.

18. The method of claim 11, wherein the at least one thioesterase enzyme comprises at least one host cell comprising a nucleotide sequence with at least 90% identity to SEQ ID NO 5.

19. The method of claim 11, wherein the at least one thioesterase enzyme comprises at least one host cell comprising a nucleotide sequence with at least 90% identity to SEQ ID NO 7.

* * * * *